(12) United States Patent
Horney et al.

(10) Patent No.: US 6,613,954 B1
(45) Date of Patent: Sep. 2, 2003

(54) DISPERSIBLE ABSORBENT PRODUCTS AND METHODS OF MANUFACTURE AND USE

(75) Inventors: James Cameron Horney, Cincinnati, OH (US); Mark Dawson Midkiff, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 20 days.

(21) Appl. No.: 09/711,475

(22) Filed: Nov. 13, 2000

Related U.S. Application Data

(63) Continuation-in-part of application No. 09/553,698, filed on Apr. 20, 2000, now abandoned.

(51) Int. Cl.$^7$ ................................................ A61F 13/15
(52) U.S. Cl. ........................................ 604/364; 604/383
(58) Field of Search ................................ 604/364, 374, 604/370, 380, 383

(56) References Cited

U.S. PATENT DOCUMENTS

| | | | |
|---|---|---|---|
| 3,343,898 A | 9/1967 | Larson | |
| 3,521,638 A | 7/1970 | Parrish | |
| 3,563,241 A | * 2/1971 | Evans et al. ............ | 160/169 |
| 3,881,210 A | 5/1975 | Drach et al. | |
| 3,886,112 A | 5/1975 | Watson et al. | |
| 3,923,592 A | 12/1975 | George et al. | |
| 3,958,574 A | 5/1976 | Rohr | |
| 4,064,880 A | 12/1977 | Logan | |
| 4,186,233 A | 1/1980 | Krajewski et al. | |
| 4,258,849 A | 3/1981 | Miller | |
| 4,360,932 A | 11/1982 | Yoshida | |
| 4,551,144 A | 11/1985 | Graber | |
| 4,575,891 A | 3/1986 | Valente | |
| 4,583,980 A | 4/1986 | Schneider et al. | |
| 4,619,862 A | 10/1986 | Sokolowski | |
| 4,668,229 A | 5/1987 | Fago et al. | |
| 4,673,401 A | 6/1987 | Jensen et al. | |
| 4,675,012 A | 6/1987 | Rooyakkers | |
| 4,734,941 A | 4/1988 | DeWitt et al. | |

(List continued on next page.)

FOREIGN PATENT DOCUMENTS

| | | |
|---|---|---|
| DE | 201008 | 10/1907 |
| EP | 0 662 310 B1 | 2/1998 |
| EP | 0 896 089 A1 | 2/1999 |
| FR | 1 258 220 | 3/1961 |
| FR | 2 04 4454 | 2/1971 |
| FR | 2 672 788 A1 | 8/1992 |
| GB | 1236904 | 6/1971 |
| GB | 2281081 A | 2/1995 |
| WO | WO 99/42068 A1 | 8/1999 |

*Primary Examiner*—Weilun Lo
*Assistant Examiner*—Jamisue A. Webb
(74) *Attorney, Agent, or Firm*—Erich D. Hemm; Leonard W. Lewis

(57) ABSTRACT

Provided are highly dispersible absorbent products, comprising an absorbent structure and preferably a water soluble barrier layer, wherein the absorbent products have a high rate of dispersibility, can exhibit low residual by-product in urinals upon flushing, resist strikethrough of absorbed fluid onto the hand of the user, and can absorb a sufficient amount of fluid without becoming overloaded or leaking. In one embodiment, provided is a ring rolled cellulosic sheet having a water soluble polymeric film laminated thereto. Also provided is a method of making such dispersible absorbent products comprising mechanically weakening an absorbent structure. Also provided are packaged products comprising a package and a plurality of dispersible absorbent products or articles. Also provided is a method for absorbing residual urine that can be both discreet and convenient, comprising absorbing residual urine subsequent to urination with a dispersible absorbent product of the present invention and depositing product in a toilet or preferably a urinal.

67 Claims, 11 Drawing Sheets

U.S. PATENT DOCUMENTS

| | | |
|---|---|---|
| 4,790,835 A | 12/1988 | Elias |
| 4,820,293 A | 4/1989 | Kamme |
| 4,863,448 A | 9/1989 | Berg |
| 4,863,655 A | 9/1989 | Lacourse et al. |
| 4,944,733 A | 7/1990 | Casale |
| 5,009,649 A | 4/1991 | Goulter et al. |
| 5,074,853 A | 12/1991 | Bryant |
| 5,143,679 A | 9/1992 | Weber et al. |
| 5,156,793 A | 10/1992 | Buell et al. |
| 5,167,897 A | 12/1992 | Weber et al. |
| 5,300,358 A * | 4/1994 | Evers ................... 428/422 |
| 5,384,189 A * | 1/1995 | Kuroda et al. ............ 428/369 |
| 5,507,906 A | 4/1996 | Woods et al. |
| 5,509,913 A | 4/1996 | Yeo |
| 5,566,400 A | 10/1996 | Jonec |
| 5,688,259 A | 11/1997 | Osborn, III et al. |
| 5,771,524 A | 6/1998 | Woods et al. |
| 5,827,255 A | 10/1998 | Crainic |
| 5,849,816 A | 12/1998 | Suskind et al. |
| 5,885,265 A * | 3/1999 | Osborn et al. ............ 604/367 |
| 6,203,654 B1 * | 3/2001 | McFall et al. ............ 156/201 |

* cited by examiner

DISPERSIBLE ABSORBENT PRODUCTS AND METHODS OF MANUFACTURE AND USE

This is a continuation-in-part of U.S. patent application Ser. No. 09/553,698, filed Apr. 20, 2000, now abandoned.

FIELD OF INVENTION

This invention is directed toward rapidly dispersible absorbent products and methods for making and using such products. This invention is especially directed toward rapidly dispersible absorbent products that are urinal flushable.

BACKGROUND OF THE INVENTION

In the anatomy of men and women, urine that collects in the bladder is excreted during the act of urination by passage through the urethra tube, ultimately exiting from the glans penis or the external urethral opening. For a high proportion of the population, a significant amount of residual urine temporarily remains in the urethral tube after urination. This occurrence is even more pronounced in males if the prostrate gland is enlarged, which restricts the flow of urine through the urethral tube. This effect, sometimes referred to as post-urinary drip, typically increases with age of the individual, and is especially common with males. Residual urine in the urethra tube eventually exits the urethra tube, though delayed subsequent to the primary excretion of urine. Residual urine also includes urine that temporarily adheres to the outer surface of the glans penis. Eventually residual urine will flow by gravity, agitation, and/or capillary action, and can soil the underclothing or trousers. In many cases, the residual urine drips during the period when the individual is dressing himself, such that the urine drips onto his clothing or onto the floor. The latter situation of dripping onto the floor is especially prevalent when the individual has urinated at an upright urinal, such as found in many public lavatories. In some cases a man may forcefully shake the penis in order to facilitate discharge of the residual urine. However in the course of shaking, the path of the urine is uncertain and the urine may contact the hands, clothing, wall and/or floor, or an adjacent person. Further, the shaking action is often only partially successful in discharging the residual urine. The situation presented by post-urination residual urine is generally unsanitary, and can lead to the spread of contagious disease. It can also cause malodor of the clothing or person, and in bathrooms, restrooms, and public lavatories, especially when usage is frequent.

Although various devices and absorbent products have been earlier disclosed to cope with this problem, such earlier expedients have been either too expensive, impractical, uncomfortable, or difficult to use. Whatever the reason for any particular device or product, the use of such devices or products has not achieved significant levels of usage in most societies. To the contrary, many people, simply allow residual urine to drip onto the floor, edge of the toilet or urinal, or their clothing. Some people use woven fabrics to wipe away residual urine and the fabric is then stored in the person's pocket or carry bag and subsequently reused. This is disadvantageous in that it requires the person to store urine-soiled material with him throughout the day. Possibly the simplest approach has been to use conventional toilet paper to absorb the residual urine. This, however, has several disadvantages. Toilet paper is often not easily accessible at public urinals that are very commonly found in men's public lavatories, but rather only located adjacent to toilets or in toilet stalls. Toilet paper also allows rapid strike-through of the urine through the thickness of the sheet, leading to wetting of the hand used to hold the paper. Finally, although toilet paper is generally flushable down a toilet, it quite often is not easily flushable down urinals, many of which have much smaller drain regions than toilets. In fact many urinals have a grid-like pattern of small orifices that make it particularly difficult to flush absorbent products down the drain. Attempts to flush toilet paper down such urinals leads to build-up of wet toilet paper in the urinal and clogging. Furthermore, toilet paper typically contains polymeric binders for providing wet strength to the sheet. These binders are important for providing the tensile strength needed for the sheets to perform well for their intended purpose. However they adversely affect the ability of the sheet to disperse into small segments or fibers that would be easily flushable down many urinal orifices and grids. Further, wet strength resins can adversely affect the toilet paper's ability to generate hydrostatic or capillary pressure. Thus, conventional toilet paper sheets are not particularly useful for use as male urinary wipes.

A variety of other approaches have been suggested for absorbing body fluids. For example, U.S. Pat. No. 5,074,853 issued Dec. 24, 1991 to Bryant discloses a male incontinence diaper. U.S. Pat. No. 5,009,649 issued Apr. 23, 1991 to Goulter, et al. discloses an expandable banded male urinary incontinence condom and supporting undergarment. U.S. Pat. No. 4,790,835 issued Dec. 13, 1988 to Elias discloses a urinary male diaper. U.S. Pat. No. 4,673,401 issued Jun. 16, 1987 to Jensen et al. discloses a male incontinence device. U.S. Pat. No. 4,944,733 issued Jul. 31, 1990 to Casaie discloses a diaper for use in toilet training male children or for use by incontinent male adults. U.S. Pat. No. 4,675,012 issued Jun. 23, 1987 to Rooyakkers discloses a method for forming an absorbent genitalia pouch for incontinent males. U.S. Pat. No. 4,064,880 issued Dec. 27, 1977 to Logan discloses a sanitary napkin for male hygiene comprising a tubular absorbent web.

These devices and others of their type may be effective for absorbing relatively large volumes of urine. However they are not practical alternatives for most people, who would not typically be receptive toward wearing diapers, condoms, or their equivalents on a continuous basis. Further, they are not necessarily designed for absorbing urine to prevent post-urinary drip. They are intended to absorb excreted urine that escapes the urethra tube and remain in place until the user removes them, often at a much later time. Thus, such users do not experience the problems associated with residual urine since the absorbent device remains in place until well after any residual urine will have been discharged.

Additionally, numerous approaches have been tried to provide flushable fibrous products for use in a variety of uses including, but not necessarily limited to, sanitary napkins, diapers, toilet seat wipes, and the like. For example: U.S. Pat. No. 5,300,358 issued Apr 5, 1994 to Evers discloses a degradable and flushable absorbent structure for sanitary napkins, diapers, and the like having an absorbent fibrous core and a backsheet comprising a cold water soluble material; U.S. Pat. No. 4,575,891 issued Mar. 18, 1986 to M. Valente discloses a small flushable toilet seat wipe of approximately 2 inches by 2 inches having a cardboard upper layer; GB Pat. No. Publication 2,281,081, published Feb. 22, 1995 by R. L. Lewis et al. discloses a web of fibrous material and polymeric binder which is said to be sufficiently hydrodisintegratable to be flushed down a toilet. The binder is applied by spraying or dipping onto wet-laid or air-laid webs. EP patent Publication 896,089 A1 published Feb. 10, 1999 by Taakeuchi et al. discloses a fibrous sheet that is disintegratable when immersed in large amounts of water comprising a fibrous sheet treated with a binder such as polyvinyl alcohol. U.S. Pat. No. 4,734,941 issued Apr. 5, 1988 to De Witt et al. discloses a flushable urine-conducting product for positioning between the legs of a female to direct urine to a receptacle. The product comprises a fibrous or non-fibrous sheet that is disintegratable in water and a water soluble polymer film. The preferred disintegratable sheet is tissue paper. U.S. Pat. No. 5,509,913 issued Apr. 23, 1996 to Yeo discloses a toilet flushable products such as diapers, fabrics, and sheets for use as wipes that are insoluble in the presence of body waste fluid but soluble in the presence of normal tap water. These patents generally address the issue of flushability in toilets, but they do not disclose products specifically designed for absorbing residual urine or post-urinary drip. They also discuss flushability from the context of toilets, as opposed to urinals, as found in most public male lavatories.

More recently, U.S. Ser. No. 09/150,476, filed Sep. 9, 1998 discloses flushable hand held absorbent devices for absorption of post urinary drip that are flushable in both toilets and urinals. It remains desirable, however, to provide absorbent products that are flushable down all types of urinals—including those with relatively large flush tubes as well as those having a plurality of relatively small orifices through which the urine must pass before being flushed out of the urinal receptacle. U.S. Ser. No. 09/235977, filed Jan. 22, 1999 discloses an absorbent device for absorbing residual urine with a transformable package.

What is needed is a convenient, easy-to-use, and easy to dispose of absorbent product that could be conveniently and discretely dispense one whenever needed, absorb residual urine, and then easily dispose of it in a convenient manner.

Therefore, it is an object of this invention to provide absorbent products useful for absorption of residual urine that are sufficiently dispersible and/or dissolvable such that they can be easily flushed through both urinals having relatively large orifices as well as urinals having relatively small orifices.

It is further an object of this invention to provide absorbent products as described above that are resistant to absorbed urine penetrating through the product and contacting the hand the user.

It is a further object of this invention to provide absorbent products as described above which can be discretely used and disposed of.

It is further an object of this invention to provide a method of making highly dispersible absorbent sheets, such as but not limited to those described above.

It is still further an object of this invention to provide a method for absorbing residual urine subsequent to urination that is both convenient and sanitary.

It is yet another object of this invention to provide devices for dispensing absorbent products suitable for absorbing residual urine which are convenient to obtain absorbent devices from prior to or subsequent to urination.

These and other objects of the invention as hereinafter described may become apparent to one of ordinary skill in the art are intended to be encompassed by the present invention in accordance with the claims which follow.

SUMMARY OF THE INVENTION

The present invention provides highly dispersible absorbent products, comprising an absorbent structure and preferably a water soluble barrier layer, wherein the absorbent products have a high rate of dispersibility, can exhibit low residual by-product in urinals upon flushing, resist strikethrough of absorbed fluid onto the hand of the user, and can absorb a sufficient amount of fluid without becoming overloaded and suffering from leakage. This invention further provides a method of making such dispersible absorbent products comprising mechanically weakening an absorbent structure. The present invention further comprises packaged products comprising a package and a plurality of dispersible absorbent products or articles. The present invention further provides a method for absorbing residual urine that can be both discreet and convenient, comprising absorbing residual urine subsequent to urination with a dispersible absorbent product of the present invention and depositing product in a toilet or preferably a urinal.

BRIEF DESCRIPTION OF THE DRAWINGS

FIGS. 3b–3c show enlarged partial perspective views of alternate embodiments of the absorbent product of FIG. 3a.

DETAILED DESCRIPTION OF THE INVENTION

Figure 1:
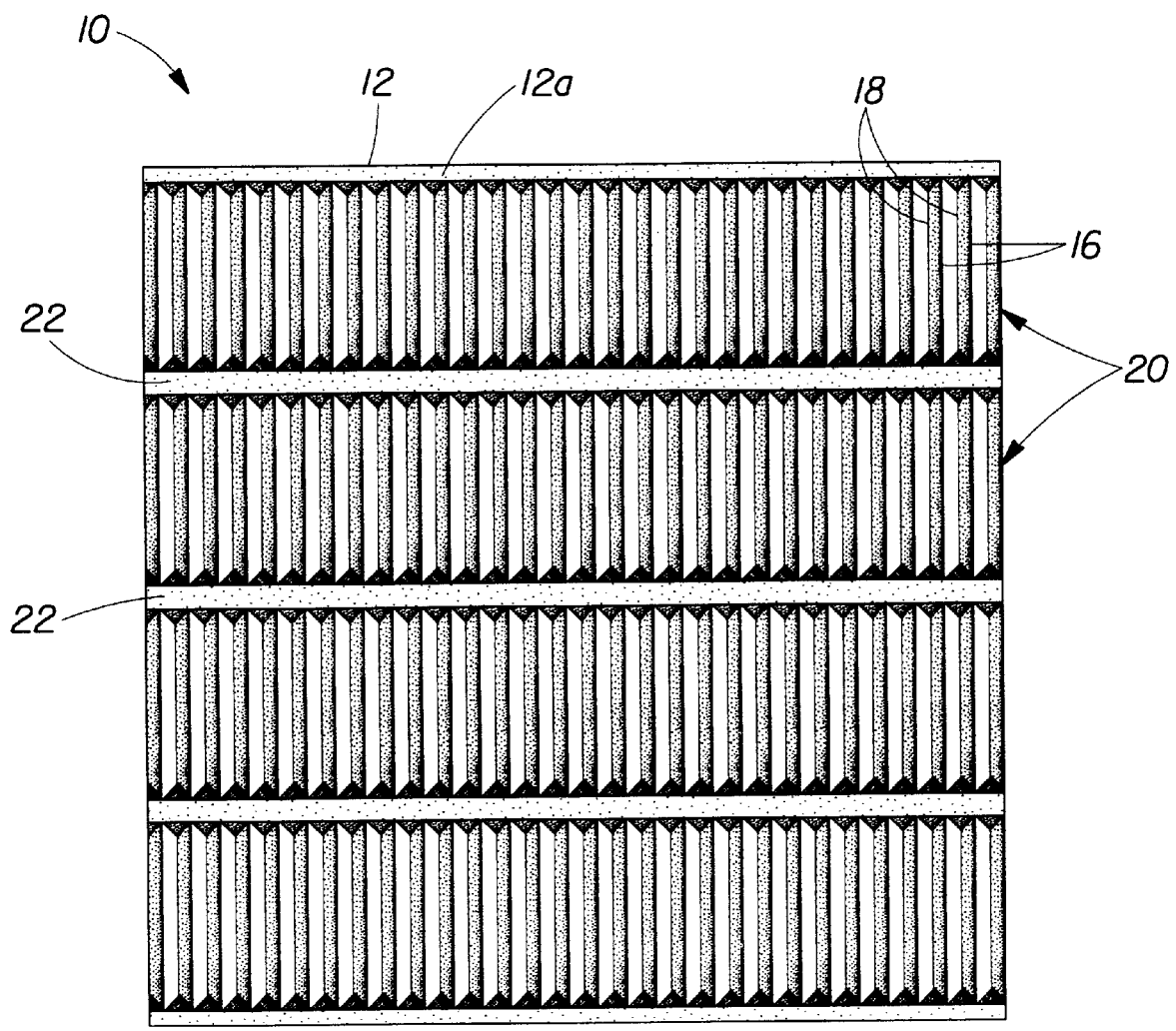
FIG. 1 shows a top planar view of an absorbent product in accordance with the present invention.

"Dispersible" as used herein means the product will break apart into smaller components or dissolve, or a combination thereof.

"Flushable" means discardable in a toilet, urinal, or other flushing device made for the purpose of receiving urine and transporting it through a plumbing system by hydraulic pressure to a sewage system.

"Residual urine" as used herein means urine remaining in the urethra tube or on the penis or labial region after urination is completed. Urination is completed when all or substantially all urine present in the bladder has been emptied from the bladder.

"Urinal" as used herein means a usually upright device intended primarily as a receptacle for receiving male urination output and disposing by flushing down a drain.

The present invention provides absorbent products that can easily and quickly disperse, are highly absorbent, and can resist strike-through of absorbed fluid to the hand of the user.

The absorbent product of the present invention can comprise an absorbent structure and a fluid barrier that may be integral with the absorbent structure or may be a distinct element and material. Preferably, but not necessarily, the fluid barrier will be a distinct element connected to the absorbent structure. The absorbent product hereof is preferably a hand-held device.

The preferred absorbent product will be in the form of a sheet. Such sheet can be of an appropriate and convenient size for storage before use, absorption of the residual urine or other intended volume of fluid, discreteness for storage and use, and ease of disposal after use. Sheets intended for absorption of residual urine preferably have a top planar surface area of from about 10 $cm^2$ to about 200 $cm^2$, more preferably from about 15 $cm^2$ to about 125 $cm^2$. Absorbent sheets for use by males preferably have a top planar surface area of from about 10 $cm^2$ to about 50 $cm^2$, more preferably from about 15 $cm^2$ to about 40 $cm^2$, most preferably from about 20 cm to about 35 $cm^2$. Also preferably the sheets for males are dimensioned such that a rectangular shape with each of four sides contacting the product at at least one point the exterior of the product has sides with lengths within the range of from about 3 cm to about 10 cm, more preferably from about 3.5 cm to about 8 cm, most preferably from about 4 cm to about 7 cm. Absorbent sheets for use by females preferably have a top planar surface area of from about 30 $cm^2$ to about 200 $cm^2$, more preferably from about 50 $cm^2$ to about 125 $cm^2$, most preferably from about 75 $cm^2$ to about 125 $cm^2$.

The sheets can have any number of shapes including but not limited to squares, rectangles, triangles, polygonals, circles, ovals, or other curvilinear shapes. The most preferred size and shape for a male residual urine absorbent sheet is a rectangle approximately 4.5 cm by 6.5 cm. The sheets can also be provided in the form a large sheet or roll having a lines of weakness included that facilitate dividing the sheet into a plurality of smaller sheets of sizes preferably within the ranges set forth above.

The thickness of the sheet can vary widely depending upon materials used, absorptive properties, basis weight, density, and construction, as well as intended use. In general, sheets intended for absorbing residual urine will preferably have a thickness of from about 0.3 mm to about 5 mm, preferably from about 0.5 mm to about 2.5 mm, more preferably from about 0.75 mm to about 2.2 mm, most preferably from about 0.8 mm to about 2 mm.

The absorbent sheets of the present invention preferably have a basis weight of from about 50 $g/m^2$ to about 250 $g/m^2$, more preferably from about 60 $g/m^2$ to about 150 $g/m^2$, most preferably from about 70 $g/m^2$ to about 120 $g/m^2$. The absorbent structure of the product as well as the entire product as a whole is preferably within these ranges. Higher or lower basis weights are not necessarily meant to be excluded, and may be desirable depending upon the intended use of the products and the means by which the product is intended to be disposed of after use.

The absorbent products hereof can also be of shapes other than sheets including without limitation three dimensional shapes such as cubes, other polygonal shapes (e.g. with four or more sides), rounded or ovalized geometric shapes (e.g. balls, wads, cylinders), etc. For absorption of residual urine, such products preferably have total exterior surface areas of from about 20 $cm^2$ to about 400 $cm^2$, more preferably from about 20 $cm^2$ to about 250 $cm^2$. For absorption of male residual urine, such products preferably have total exterior surface areas of from about 20 $cm^2$ to about 100 $cm^2$, more preferably from 30 $cm^2$ to about 60 $cm^2$. For absorption of female residual urine, such products preferably have total exterior surface areas of from about 60 $cm^2$ to about 400 $cm^2$, more preferably from about 100 $cm^2$ to about 250 $cm^2$, most preferably from about 150 $cm^2$ to about 250 $cm^2$.

It is critical feature of disposable products, and especially of absorbent products intended to be flushed down urinals or other easily cloggable flushing devices, that disposal of the products not cause clogging. It is further important that the absorbent product not excessively collect in the receptacle of the urinal upon multiple uses. This is especially important in public lavatories that experience high levels of use. The absorbent products according to the present invention therefore are highly dispersible. Preferably the absorbent products of the present invention will have a "Rate of Dispersibility", as determined according the Rate of Dispersibility Test described below in the Test Methods section, of 120 seconds or less, more preferably 60 seconds or less, more preferably 30 seconds or less, more preferably 25 seconds or less, and most preferably 15 seconds or less. There is no absolute lower limit for Rate of Dispersibility, except that the product should retain sufficient cohesiveness during use so as to not prematurely disperse or otherwise lose integrity during manufacture, storage, dispensing, or use prior to disposal in the urinal or other intended receptacle. Rate of Dispersibility will typically be 5 seconds or greater.

In addition to being highly dispersible, the dispersed products should be capable of flowing through the orifices they will be flushed through subsequent to use. It is desirable that male residual urine absorbent products be flushable down urinals having drainage orifices of 10 mm diameter and smaller, preferably 8 mm diameter and smaller.

With respect to absorbent structures made from fibrous material or other non-dissolvable material, for example, the structure should disperse into individual fibers or into discrete flushable sections of fibers, with such sections still retaining cohesiveness but being sufficiently small and/or conformable to pass through small orifices. As used herein, "sections" of fibers can include uniformly (for example, but not limited to, squares) or non-uniformly (for example, but not limited to, chunks, agglomerations, etc.) shaped sections of fibers. Aqueous slurries of fibers shall be considered as containing a plurality of individualized fibers or sections of fibers, as the case may be. Fibers may be longer in length than the orifices and still be flushable so long as they are sufficiently dispersed from one another that they retain sufficient flexibility to fit through the orifices under the pressures conventionally experienced during flushing and do not block or clog the orifices. Nonfibrous materials that disperse into discrete sections rather than dissolving should be small enough to fit through the dimensions of the orifices.

A wide variety of urinal drain orifice shapes and sizes exist. By urinal drain orifice, what is meant is the size one or plurality of orifices through which urine and the absorbent products of the present invention must flow through in order to be flushed into a septic, sewer, or other waste handling system. Whereas some urinals have one, relatively large orifice, others have a plurality of much smaller orifices. Urinal grids are commonly placed over the integral urinal drain, thereby effectively reducing the size of the orifice through which product must pass through. Materials that are used in the present invention preferably dissolve or disperse into sections that have a cross-section that can be enclosed by a rectangle having a maximum side length of about 30 mm or less, more preferably about 20 mm or less, more preferably about 15 mm or less, more preferably about 10 mm or less, more preferably about 6.5 mm or less, more preferably about 4 mm or less, most preferably about 3 mm or less. Similarly, without limitation, the urinal orifices through which the products hereof are flushed can have orifice cross-sectional diameters of 30 mm or less, 20 mm or less, 15 mm or less, 10 mm or less, 6.5 mm or less, 4 mm or less, or 3 mm or less. Preferably the absorbent product sections have cross sections that are slightly smaller than the size of the orifice through which it must pass.

Preferably the absorbent products are sufficiently dispersible to flow through a U.S.A. Standard Testing Sieve (A.S.T.M. E-11 Specification) having rectangular openings of 0.25 inches by 0.25 inches (about 6.3 mm by 6.3 mm) in accordance with the Residual By-Product Test hereinafter discussed. Preferably, the products hereof will have Residual Product Levels in accordance with such test of about 60% or less, more preferably about 50% or less, even more preferably about 25% or less, even further preferably about 10% or less, and most preferably about 5% or less. It has been found that when the Residual Product Level is sufficiently low, product accumulation after multiple disposals into a urinal is minimized, and preferably after several flushes without additional absorbent product the residual product remaining in the urinal is substantially removed.

The preferred absorbent products of the present invention also absorb the intended volume of fluid without suffering from over-saturation or "strikethrough". By "strikethrough" what is meant is that fluid absorbed during use flows to the opposite side of the product, or to such other portion of the product that is used to hold the device in place during use, and is able to contact directly a material that is positioned against, adjacent to, or holding the product. This can, for example, be the opposite side of a sheet that is held in place by the user's hand. The preferred absorbent products of the present invention have Strikethrough Resistance as determined according to the Strikethrough Test described below in the Test Methods of at least 2 seconds, preferably at least 10 seconds, more preferably at least 30 seconds. The absorbent products of the present invention are also highly absorbent. Such products should be highly absorbent of the type of fluid they are intended to absorb during actual use. Additionally, for purposes such as absorbing residual urine, in some preferred embodiments of the present invention the products generate relatively high levels of hydrostatic pressure in addition to having high total absorption capability. Absorbent products that generate high hydrostatic pressure are more capable of competing with hydrostatic pressure generated by surface pores of the surfaces from which it is intended to absorb fluid, as well as compete more effectively to absorb fluid held in small apertures, including body channels such as the urethra tube.

Absorption properties of absorbent products can be described according to their absorption capacity at different levels of hydrostatic pressure. Absorption capability for purposes of the present invention is determined in accordance with this principle by the Pore Volume Distribution (PVD) test described below in the Test Methods section. Total absorption capability of the products hereof is measured by the PVD test at zero (0) cm hydrostatic head, PVD(0) at the end of the absorption cycle. The ability of the absorbent products hereof to generate hydrostatic pressure is measured by the PVD test at 7.0 cm hydrostatic head, PVD(7) as peak absorption on the absorption side of the absorption/desorption cycle. The absorbent products of the present invention should preferably have PVD(0) of at least about 2.0 g fluid/g product, more preferably at least about 2.5 g/g, more preferably at least about 3.0 g/g, most preferably at least about 4.0 g/g. Typically, although not necessarily, the PVD(0) will be up to about 8.0 g/g. The PVD(7) is preferably at least about 1.5 g/g, more preferably at least about 2.0 g/g, more referably at least about 2.5 g/g, most preferably at least about 3.0 g/g. Typically, although not necessarily, for many types of structures such as fibrous webs, the PVD(7) will be up to about 5.0 g/g. In the preferred embodiments hereof, the PVD(7) is in the range of from about 60% to about 85%, more typically from about 70% to about 80%, of the PVD(0). It has been found that absorbent fibrous structures subjected to mechanical weakening processes, such as ring rolling can improve both PVD(0) and PVD(7).

As is well known and understood in the art, total absorption capability is dependent upon the choice of structural materials (chemistry and shape of the material and topography of the material surface), contact angle of fluid on the absorbent structure surface, and pore volume distribution of the structure. Capillary or hydrostatic pressure of absorbent products can be enhanced by methods well-known in the art such as, but not limited to, surface treatments of the absorbent element, adjusting pore size, density, and fiber length in absorbent elements. Products used for purposes such as absorbing residual urine preferably should have an absorptive capacity sufficient to absorb the amount of residual urine typically remaining after urination. In general, the absorbent product intended for use to absorb residual urine from a male preferably should be able to absorb at least 0.2 ml of urine, more preferably at least 0.5 ml, even more preferably at least 0.7 ml, most preferably at least about 1.0 ml. It has been found that absorption capacity of 1 ml is sufficient for complete absorption of residual urine for most males individuals, although higher levels of absorption are not meant to be excluded.

The preferred absorbent products of the present invention can quickly absorb fluid deposited onto the surface of the products. Furthermore, in many circumstances, the products hereof will be used under circumstances wherein fluid will contact the absorbent product at an angle diverging from the horizontal. Therefore the preferred absorbent product of the present invention quickly absorb the fluid coming into contact with it without unabsorbed fluid running down the surface of the product. The ability of the absorbent products hereof to quickly absorb fluid without unabsorbed fluid run-off can be measured according to the Drop Acquisition Test, which is described in the Test Methods section below. Preferred absorbent products of the present invention have a Drop Acquisition Volume according to the Drop Acquisition Test of at least about 0.05 ml, preferably at least about 0.1 ml, more preferably at least about 0.50 ml., most preferably at least about 1.0 ml.

The absorbent structure can be made from any material capable of absorbing fluids, such as urine and other aqueous fluids. These include natural and synthetic fibers, foams, sponges, natural absorbent materials such as peat, and absorbent porous polymeric macrostructures comprising inter-particle cross-linked aggregate. Preferred materials include fibers and foams. Suitable synthetic fibers include fibers made from polypropylene, polyethylene, and polyester, polyacrylates, and copolymers thereof and mixtures thereof. Derivatives, homologs, and analogs thereof are meant to be included in the above materials. Co-form fibers such as those with a sheath and core construction of separate polymeric materials, or of a bias construction with two separate materials are also meant to be included. Fibers that are hydrophobic may be treated with wetting agents in order to facilitate absorption of aqueous liquids. Capillary channel fibers may also be used. Capillary channel fibers are fibers having internal or external capillary channels that facilitate wicking of fluids. Capillary channel fibers are disclosed, for example in U.S. Pat. No. 5,200,248 issued Apr. 6, 1993 to Thompson et al., incorporated herein by reference.

Fibrous absorbent structures can be woven or nonwoven, preferably nonwoven. Nonwoven absorbent structures can be wet laid or air laid. Preferably wet laid nonwoven absorbent structures are mechanically weakened by incorporation of lines of weakness or application of other structural weakening processes such as ring rolling and its variants, as further described below.

Natural fibers include cellulosic fibers and derivatives thereof. Suitable cellulosic fibers include those derived from any tree or vegetation, including hardwood fibers, softwood fibers, hemp, and cotton, as well as fibers made from processed natural cellulosic resources such as rayon, and combinations thereof. Preferred hardwood fibers include eucalyptus fibers. Preferred hardwood fibers are prepared by kraft or other chemical pulping methods. Suitable softwood fibers include southern softwood (SS) fibers and northern softwood (NS) fibers. Softwood fibers for use herein can be chemically (e.g., without limitation, kraft pulp) or mechanically pulped (e.g., without limitation, chemithermal mechanical pulp (CTMP) and thermal mechanical pulp (TMP)). Preferred softwood fibers include chemically pulped SS fibers, such as southern softwood kraft (SSK), and mechanically pulped NS fibers, such as northern softwood chemithermal mechanical pulp (CTMP) and thermal mechanical pulp (TMP). Unblended fibers can be used herein. However preferred for use herein are combinations of hardwood fibers and softwood fibers. When combinations of hardwood and softwood fibers are used, the absorbent structure will preferably contains from about 5% to about 75%, by absorbent structure weight, hardwood fibers, more preferably from about 5% to about 50%, most preferably from about 10% to about 20%, and from about 25% to about 95%, by absorbent structure weight, softwood fibers, more preferably from about 50% to about 95%, most preferably from about 80% to about 90%. Also preferably the absorbent structure comprises a mixture of SSK and northern softwood (NS) fibers (CTMP or TMP, preferably CTMP). Preferably the absorbent structure comprises from about 5% to about 75%, by absorbent structure weight, northern softwood (CTMP or TMP), more preferably from about 5% to about 50%, most preferably from about 15% to about 40%, and from about 20% to about 85% southern softwood fibers, more preferably from about 45% to about 85%. An especially preferred blend contains about 15% hardwood, about 40% NS CTMP, and about 45% SSK.

Shorter length fibers, such as the hardwood fibers, provide improved dispersibility and flushability of the absorbent products. Softwood fibers tend to be longer than hardwood, and can enhance tensile strength and product integrity, as well as provide better softness and greater absorbent capacity than hardwood fibers. It is preferred that the absorbent structures have an average fiber length of about 7 mm or less, more preferably about 5 mm or less, more preferably about 4 mm or less, more preferably about 3.5 mm or less, most preferably about 3 mm or less. With respect to absorbent products which at least partially rely upon tensile strength of the absorbent structure for product integrity during manufacturing or use, it is preferred that the average fiber length be at least about 0.5 mm, preferably at least about 0.9 mm, more preferably at least about 1.5 mm, most preferably at least about 2 mm. Average fiber length as used herein determined on a number average basis, such as measured by a Kajaani FS-200 Fiber Analyzer (available from Valmet, Norcross, Ga., USA) or equivalent.

The absorbent structure can also comprise an absorbent foam. Absorbent foams suitable for use in the present invention are described in: U.S. Pat. No. 5,260,345 issued to DesMarais, et al. on Nov. 9, 1993; U.S. Pat. No. 5,268,224 issued to DesMarais et al. on Dec. 7, 1993; U.S. Pat. No. 5,387,207 issued to Dyer et al. on Feb. 7, 1995; U.S. Pat. No. 5,550,167 issued to DesMarais on Aug. 27, 1996; U.S. Pat. No. 5,563,179 issued to Stone, et al. on Oct. 8, 1996; U.S. Pat. No. 5,650,222 issued to DesMarais et al. on Jul. 22, 1997; and U.S. Pat. No. 5,649,920 issued to Dyer et al. on Jul. 22, 1997; all being hereby incorporated by reference.

Porous absorbent polymeric macrostructures comprising inter-particle cross-linked aggregate are described in: U.S. Pat. No. 5,124,188 issued to Roe et al. on Jun. 23, 1992; U.S. Pat. No. 5,180,622 issued to Berg e al. on Jan. 19, 1993; and U.S. Pat. No. 5,330,822 issued to Berg et al. on Jul. 19, 1994; all incorporated herein by reference.

The preferred absorbent products of the present invention, as previously described, are effective at inhibiting strike-through of fluid from to opposite side of the product, in the case of a sheet product. Therefore, the preferred products hereof have a barrier layer which provides at least temporary resistance to strike-through. Temporary resistance against strike-through can be determined according to the Strikethrough test, as previously discussed. Enhanced resistance against strike-through as well as improved product structural integrity and tensile strength prior to saturation is preferably achieved through use of a barrier layer in the form of water soluble polymeric material, such as a polymeric film or foam, preferably a film. Suitable polymeric film materials include polyvinyl alcohol (PVA), polyethylene oxide (PEO), polyethylene glycol (PEG), hydroxy lower alkyl (methyl, ethyl, and propyl, and combinations thereof) celluloses, and starch, preferably polyvinyl alcohol. Polymeric films can have, but are not limited to, thicknesses of from about 15 microns to about 60 microns, preferably from about 20 microns to about 50 microns, more preferably from about 30 microns to about 45 microns, most preferably from about 35 microns to about 40 microns. Preferred polyvinyl alcohol polymer films suitable for use herein include MONO-SOL ™ E-6030C and M-8630 (Chris Craft Industrial Products, Inc., Gary, Ind., USA). The water soluble polymeric material can also be sprayed onto the surface of the absorbent structure. Still further barrier materials include water insoluble polymers which can be sprayed onto the absorbent structure. Suitable examples include latex, temporary wet strength resins, and starch. Specific examples include: melamine formaldehyde and urea formaldehyde resins, such as available under PAREZ™ series from Cytec Industries, Inc., West Patterson, N.J., USA; polyamide-epichlorohydrin resins; polyacrylamide-glyoxal resins; and polyethylenimine resins; and others as can be found in TAPPI monograph series No. 29, Wet Strength in Paper and Paperboard, Technical Association of the Pulp and Paper Industry (New York, 1965), incorporated herein by reference. Starches include cationic starches. Other materials include polyacrylic acid and polyvinyl acetate. When water insoluble barrier materials are used, the barrier material should be discontinuous, which can be accomplished by spraying in a discontinuous pattern or manner, in the form of droplets at relatively low levels of application such that the degree of continuity remains low, or by incorporating lines of weakness into the barrier layer.

As described above, absorbent products of the present invention should have sufficient dispersibility characteristics in order to easily disperse upon disposal, especially in aqueous conditions. However most absorbent structures having good absorption characteristics will not be sufficiently dispersible for purposes of this invention. Improved dispersibility can be achieved by a variety of techniques. Without limitation, these include a variety of techniques for mechanically weakening the absorbent structure such as by partially disentangling fibers of an absorbent fibrous web, and/or by incorporation into the absorbent structure of regions of weakness. Regions of weakness include but are not limited to continuous regions of weakness (including but not limited to continuous lines of weakness) and discontinuous regions of weakness (including but not limited to random or patterned regions of weakness separated by a continuous region having greater tensile strength than the regions of weakness). Continuous lines of weakness include but are not limited to slits and linear regions (or "lines") of stretched or partially disentangled regions of the absorbent structure or fibers within the absorbent structure. Discontinuous regions of weakness include but are not limited to slits and perforations, as well as regions of stretched or lower density absorbent structure, or partially separated fibers, surrounded by higher density regions the absorbent structure. As used herein, "discrete sections" of the absorbent structure refers to sections of absorbent structure that are separated from adjacent discrete sections by regions of weakness. In one embodiment, the discrete sections of absorbent structure are separated by lines of weakness that extend through the entire thickness of the web, such that elements of the absorbent structure do not bridge the gap between adjacent sections. In another embodiment, the lines of weakness are cuts or slits extending partially through the thickness of the absorbent structure. In yet another embodiment the lines of weakness are low density lines of weakness wherein fibers bridge the gap across the line of weakness between adjacent sections, albeit at lower density than the adjacent sections. In another embodiment the lines of weakness are lines of partially disentangled fibers. Fibrous webs, especially nonwoven webs, can be mechanically weakened by partially disentangling fibers. This can be done either throughout the entire web, or through portions of the web while retaining portions of non-disentangled fibers. Partial disentanglement of web material fibers can be accomplished by any methods as may be known in the art, preferably but not limited to passing the web through a nip between grooved or patterned rolls—a process which has been described as pre-corrugating or "ring-rolling", such as described in U.S. Pat. No. 4,107,364 issued to Sisson on Aug. 15, 1978; U.S. Pat. No. 5,143,679 issued to G. M. Weber et al. on Sept. 1, 1972; U.S. Pat. No. 5,156,793 issued to K. B. Buell et al. on Oct. 20, 1992; and U.S. Pat. No. 5,167,897 issued to G. M. Weber et al. on Dec. 1, 1992; all incorporated herein by reference. Ring-rolling has the effect of elongating the absorbent structure, thereby partially disentangling them, and typically also decreasing density and increasing softness and maximum absorption (e.g., PVD (0)). Preferred, modified ring rolling methods are described in WO 95/037675 (PCT/US94/08249), Chappel, C.W. et al., published Feb. 9, 1995, incorporated herein by reference. Preferably, a sheet of both the absorbent web and water soluble barrier layer, such as but not limited to a water soluble polymeric film, is ring-rolled. A polymeric film barrier layer can also limit the degree of elongation during ring rolling and can provide a degree of elasticity to the absorbent product, depending upon the elastic properties of the polymeric film.

Fibrous and non-fibrous absorbent structures can have lines of weakness incorporated therein to aid dispersibility. By lines of weakness what is meant is that the structure includes a lines such as but not limited to intermittent slits (i.e. discontinuous slits or perforations) or continuous slits, either of which extend at least partially, and optionally entirely through, through the thickness of the absorbent structure. Processes such as ring rolling operate to either impart slits (generally continuous lines of weakness) or continuous lines of weakness characterized by partially separated fibers, wherein in the latter case the web is stretched during ring rolling to reduce density of the fibers in the stretched region. With respect to products having noncontinuous non-water soluble barrier layers, lines of weakness preferably extend through the barrier layer. One method of making such structures is to mechanically weaken the absorbent structure subsequent to initial formation by incorporating lines of weakness. Alternately the absorbent structure can have lines of weakness incorporated when the absorbent structure is formed.

In one preferred embodiment, the lines of weakness extend more than 50% through the thickness of the absorbent structure, optionally through the entire thickness of the absorbent structure. Such lines of weakness are preferably in the form of continuous slits.

Regions of weakness can be incorporated into the absorbent products by numerous techniques, as will be apparent to those skilled in the art. Without limitation, suitable ways to introduce regions of weakness such as lines of weakness include cutting or slitting the product with a blade, forming the absorbent structure initially with lines of weakness incorporated therein, such as by a pattern forming wire or web as used in paper making processes, or ring-rolling products under conditions wherein high tension points of the sheet break, or crack, during processing. Ring-rolling under these conditions depends upon the type of sheet material treated, pitch of the ring roll teeth, and degree of engagement of the opposing teeth of the rolls. In particular, it has been found that use of a high proportion of short fibers or all short fibers, such as hardwood fibers or fibers with average fiber lengths of about 2 mm or less, are preferred for ring rolling processing wherein it is desired to introduce lines of weakness in the form of slits partially extending through the thickness of the absorbent structure, and especially for lines of weakness extending through at least 50% of the thickness or through the entire thickness of the absorbent structure.

In another preferred embodiment, regions of weakness are provided in the form of lines of weakness characterized by partially detangled fibers, or partially separated fibers, of lower density compared to the adjacent regions of higher tensile strength and density. Such products can be made by ring rolling as previously described. In particular it has been found that the use of long fibers, such as softwood fibers, or blends of such long fibers with short fibers, are preferred for ring rolling to make products with such partially detangled fibers in the form of lines of weakness. Additionally, in accordance with the ring rolling process as further discussed below, incorporation of increased levels of water in the web during the ring rolling step can further contribute to the fibrous web stretching to form reduced density fibrous regions as opposed to forming slits through the fibrous web. In general, it is preferred to include from about 0.0001 ml/square cm to about 0.004 ml water/square cm web surface during ring rolling for products desired to have regions of weakness in the form of low density lines of partially detangled fibers.

Particularly but not limited to embodiments wherein the lines of weakness extend through the thickness of the absorbent structure to a degree that cohesive of the sheet in the absence of the barrier layer would be insufficient to maintain integrity of the sheet during manufacture, storage, or use, the barrier layer can provide cohesiveness to the absorbent sheet. This is particularly the case when the lines of weakness are cuts extending substantially or completely through the thickness of the absorbent structure.

Figure 2:
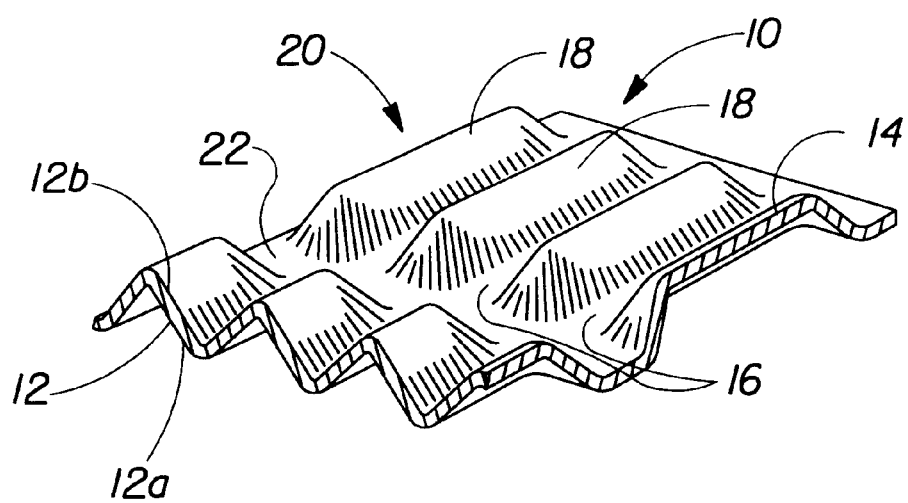
FIG. 2 shows a bottom perspective view of a portion of an absorbent product in accordance with the present invention.

Referring now to FIGS. 1–2, shown is a preferred embodiment of the present invention. The absorbent product 10 is in the form of a sheet having a web material 12 of absorbent cellulosic fibers, having a top surface 12a, a bottom surface 12b, and a barrier layer 14 (see FIG. 2) adhered to the bottom surface 12b. The barrier layer 14 is a thin water soluble polymeric film such as polyvinyl alcohol (PVOH) or other water soluble polymeric material. Barrier layer 14 is laminated to the bottom of absorbent structure 12 and closely follows the same topographical profile as the absorbent structure 12. Barrier layer 14 is thin in preferred embodiments and therefore the thickness of such layer is not necessarily easily discernable to the naked eye, though it is graphically displayed in FIG. 2. The web material includes a plurality of rows 20 of ridges 16 and valleys 18. The topography of the bottom surface 12b of the absorbent product 10 is the opposite of the top surface 12a. Ridges 16 of the top surface 12a would correspond to valleys in on the bottom surface 12b. The ridges 16 and valleys 18 can be formed as a result of ring rolling, preferably by ring rolling a laminate of the absorbent web 12 and barrier layer 14. Rows 20 are separated by strips 22. Strips 22 are approximately the same height as ridges 16 of the top surface 12a. Correspondingly, if viewed from the bottom side of the absorbent product 10, strips 22 would appear as grooves. Strips 22 are optional features of the present invention and are not necessarily present in the absorbent product 10. The bottom perspective view of FIG. 2 further shows how ridges 66 and valleys 68 of the absorbent product 10 create a three dimensional topography. FIG. 2 further shows a strip 22 portion. Strips can be introduced through the use of ring rolling techniques, as further disclosed below.

As previously discussed, partial disentanglement of fibers in web 12 fibers can be accomplished by any methods as may be known in the art including, preferably, ring rolling such as described in WO 95/037675 (PCT/US94/08249), Chappel, C.W. et al., published Feb. 9, 1995. The web 12 or absorbent structure can be connected to the polymeric film barrier layer 14 of the present invention by any method known in the art. Preferably the polymeric film is adhered to the absorbent structure, most preferably laminated. Films can be adhered to absorbent structures through the use of water soluble adhesives. Preferably the absorbent structure is adhered directly to a water soluble film without the use of a separate adhesive, such as by partially solubilizing the surface of the film with water, contacting the absorbent structure with the film either before or after partial solubilization, and then allowing the film to dry or drying the film. Preferably the absorbent structure and partially solubilized film are pressed against one another (bonding pressure), to facilitate forming a laminated product. The moistened film partially dissolves when wet then hardens as it is dried adhering portions of the absorbent structure in direct contact with the dissolved portion of the film, thereby forming a laminated sheet.

Figure 4:
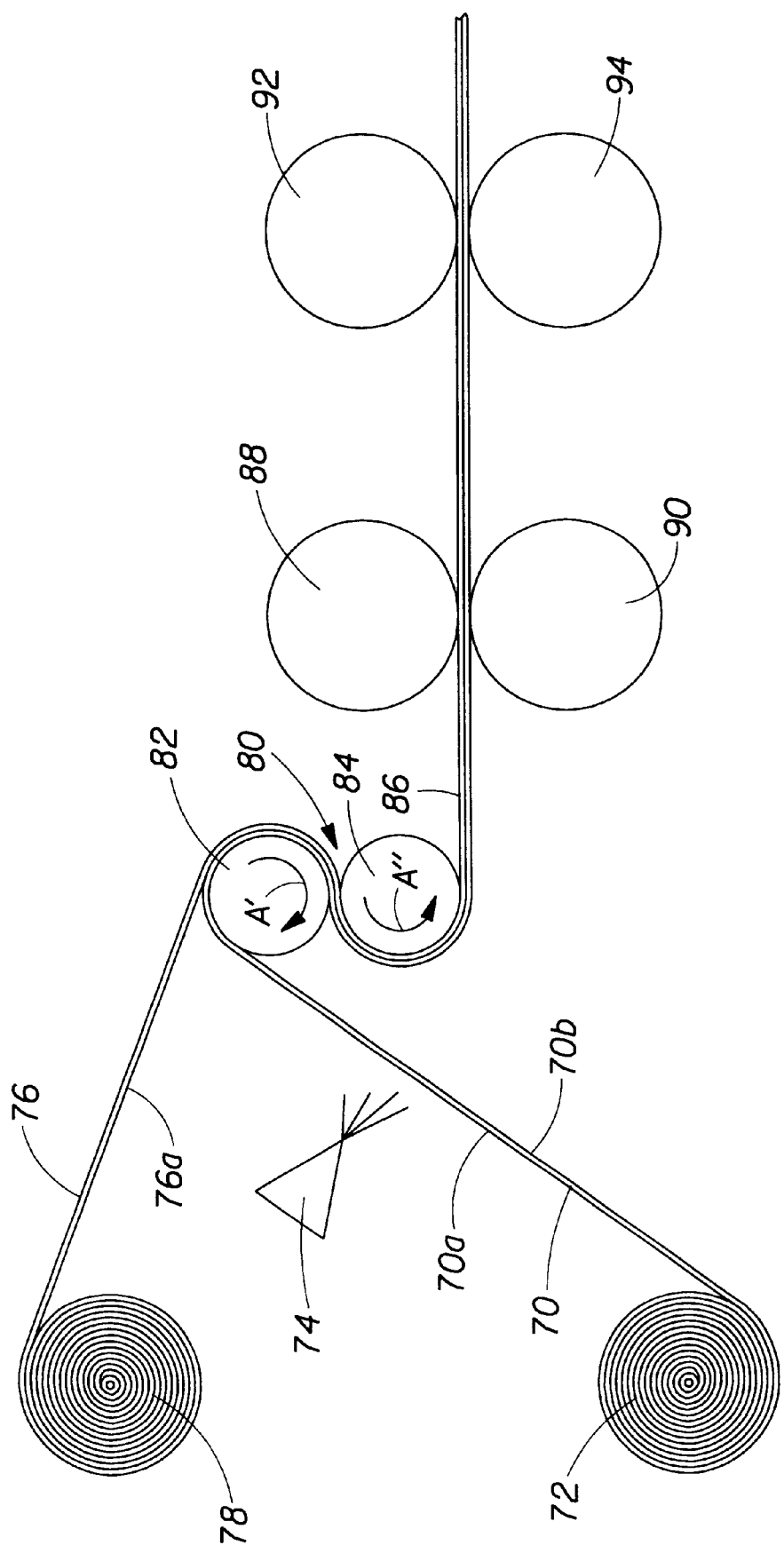
FIG. 4 shows a flow chart for a method of manufacturing an absorbent product of the present invention.

Referring to FIG. 4, a preferred method of making an absorbent structure, suitable for making products such as shown in FIGS. 1–2 is shown. In this continuous process an absorbent web 70 from web roll 72 is sprayed on the top surface 70a with water by sprayer 74 and proceeds to a heated roll 82 of laminator 80. A water soluble polymeric film 76 is unwound from film roll 78 and proceeds to heated roll 82 of laminator 80. Bottom surface of web 70b directly contacts the heated roll 82. Top surface of web 70a contacts and is adjacent bottom surface 76a of film 76, to form a bi-layer sheet 86 that travels around heated roll 82 in the direction indicated by A' to heated roll 84 of laminator 80, rotating in the direction indicated by A". The bi-layer sheet travels between heated rolls 82 and 84, which compress and laminate film 76 to web 70. Heated rolls are heated to dry the sheet 86 of water applied by sprayer 74. Heated roll temperature is preferably from about 120 C to about 160 C. The laminated bi-layer sheet is mechanically weakened in a first ring rolling stage by passing between ring rolls 88 and 90 and optionally, and preferably, through a second ring roll stage by passing between ring rolls 92 and 94.

Figure 5:
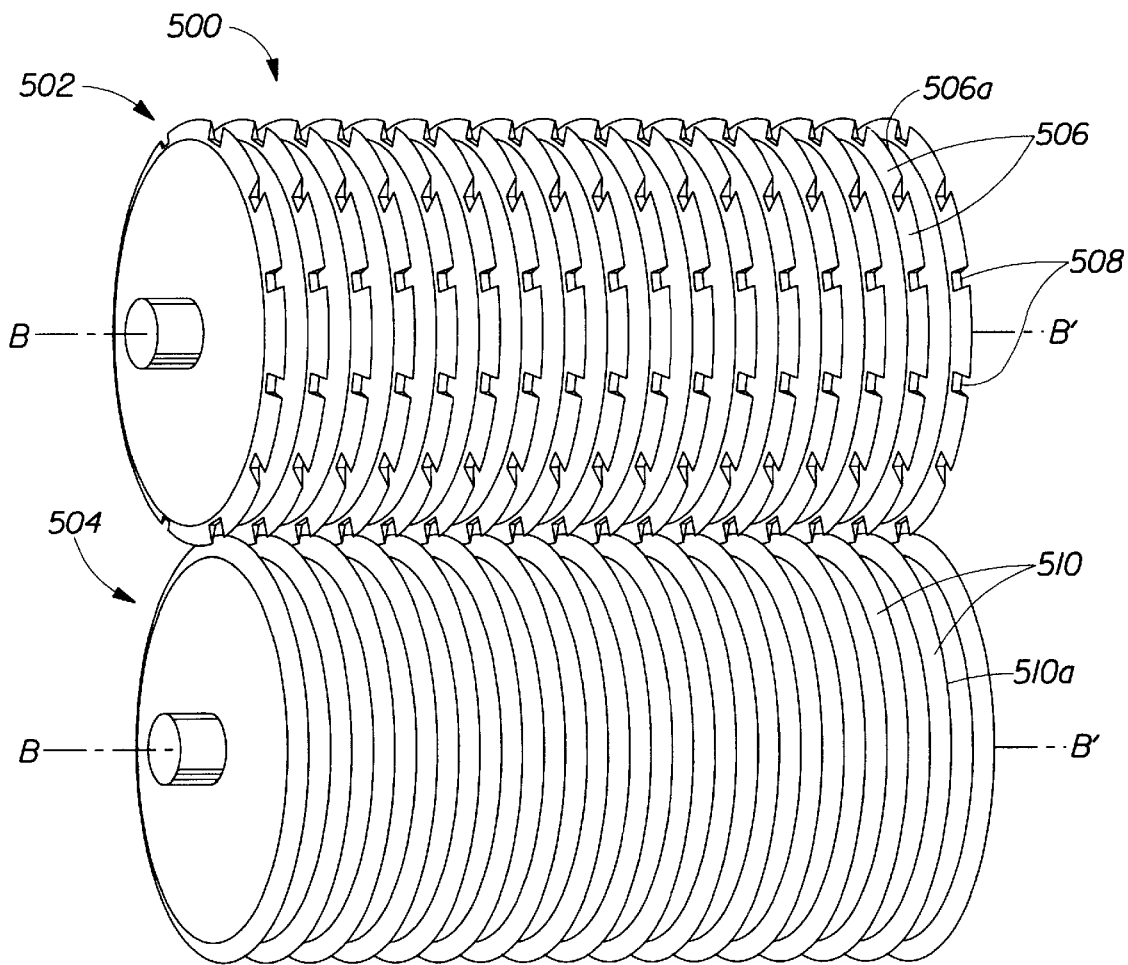
FIG. 5 shows a set of ring rolls useful for manufacture of absorbent products of the present invention.
Figure 6:
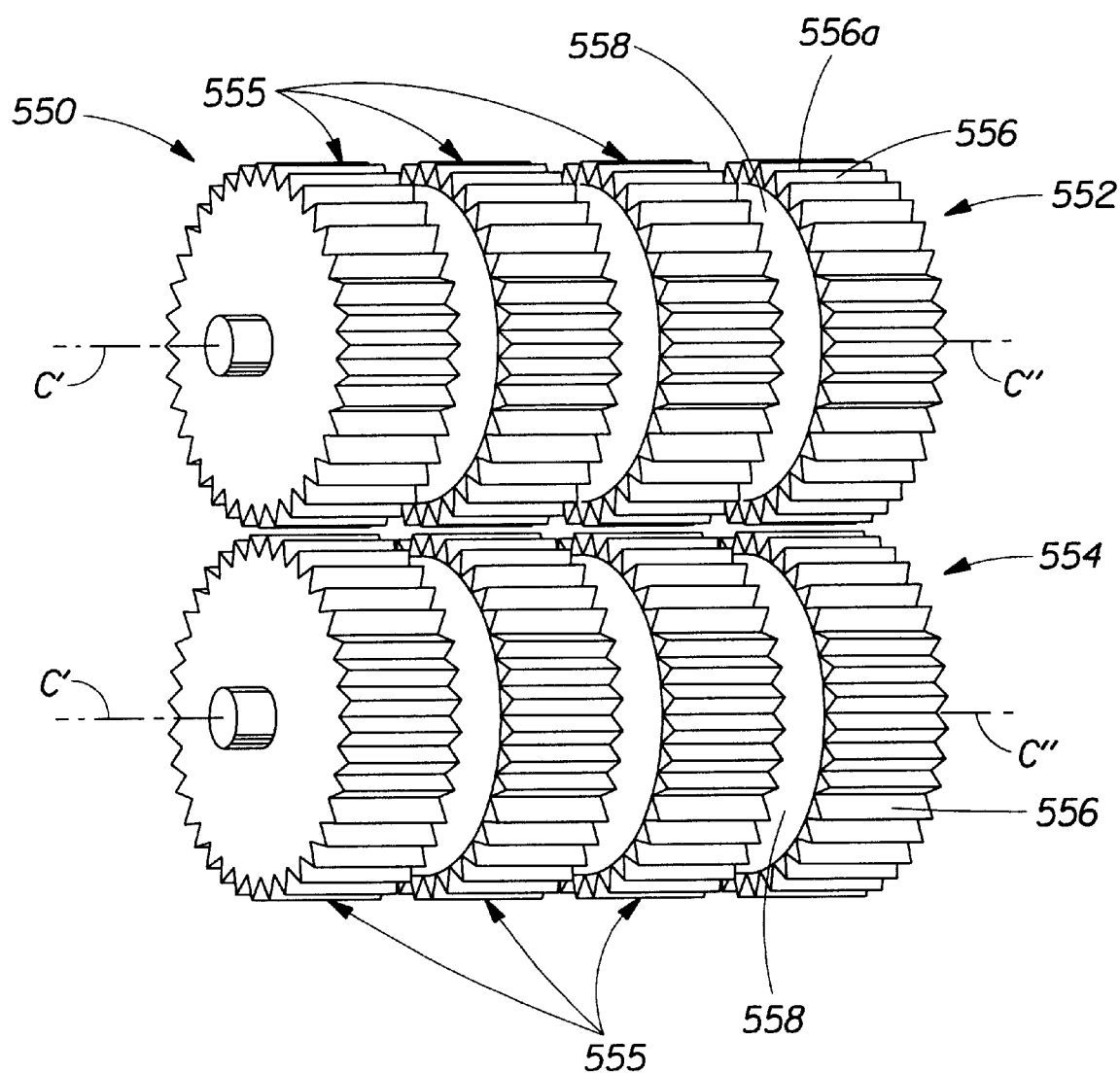
FIG. 6 shows an alternate set of ring rolls useful for manufacture of absorbent products of the present invention.

Referring now to FIG. 5, shown is a pair of preferred ring rolls 500 having upper ring roll 502 and lower ring roll 504, which are suitable for use in the method shown in FIG. 6. Ring roll 502 has circular rows of teeth 506 with ridge lines 506a extending perpendicularly to the longitudinal axis of the roll B–B'. The rows of teeth 506 have notches 508, which impart the pattern of strips 22 of non-mechanically weakened fibers of FIGS. 1–2. Notches 508 are optional features of the process and products of the present invention. Notches can create a pattern effect in the finished absorbent structure. As shown in FIG. 5, lower ring roll 504 has rows of teeth 510 having ridge lines 510a extending perpendicularly to the longitudinal axis of the roll B–B' that do not have notches. Ring rolls 502 and 504 are aligned during use such that rows of teeth 506 are aligned approximately mid-point between rows of teeth 510.

Specific ring rolling parameters can vary widely according to the specific materials utilized and degree of mechanical weakening desired. Ring rolling conditions that can be used are described, for example in the ring rolling references discussed above and incorporated herein by reference. For preferred embodiments of the present invention, the spacing between rows of teeth in the B–B' direction is from about 0.04 inches (about 0.1 cm) to about 0.5 inches (about 1.27 cm), more preferably from about 0.07 (about 0.18 cm) inches to about 0.2 (about 0.51 cm) inches, more preferably from about 0.09 (about 0.23 cm) inches to about 0.15 inches (about 0.38 cm); most preferably about 0.1 (about 0.25 cm) inches; depth of the teeth is from about 0.08 inches (about 0.20 cm) to about 0.25 inches (about 0.64 cm), preferably from about 0.08 (about 0.20 cm) inches to about 0.18 inches (about 0.46 cm); pitch of the teeth is sufficient in view of the web thickness and other ring roll dimensions such that the web is not pinched between the teeth during processing.; and degree of engagement between teeth of the opposing ring rolls is from about 0.015 inches (about 0.038 cm) to about 0.15 inches (about 0.38 cm), preferably from about 0.02 inches (about 0.051 cm) to about 0.08 inches (about 0.20 cm). The above parameters are preferred however are not meant to exclude selection of lower or higher values for use in making products otherwise in accordance with the present invention.

The mechanically weakening methods hereof, including both partial disentanglement and incorporation of lines of weakness may be applied to both absorbent structures with or without a barrier layer. However in the case of lines of weakness extending throughout the entire width of the structure, or through substantially the entire width, a barrier layer preferably will be present prior to incorporation of such lines of weakness.

Figure 3A:
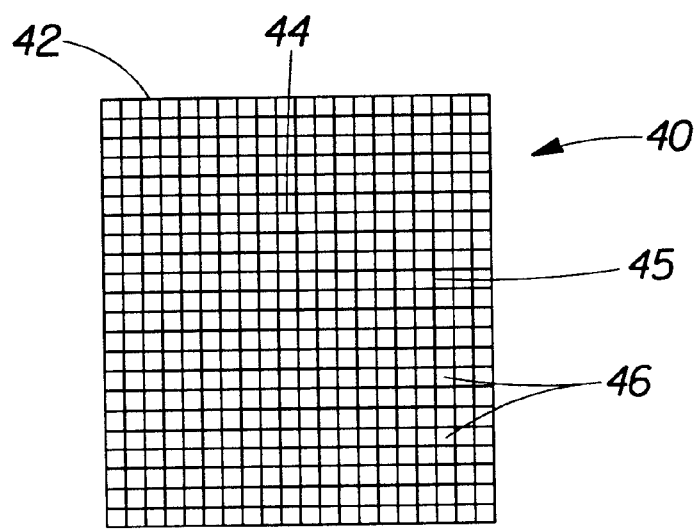
FIG. 3a shows a top planar view of an alternate embodiment of an absorbent product of the present invention.
Figure 3B:
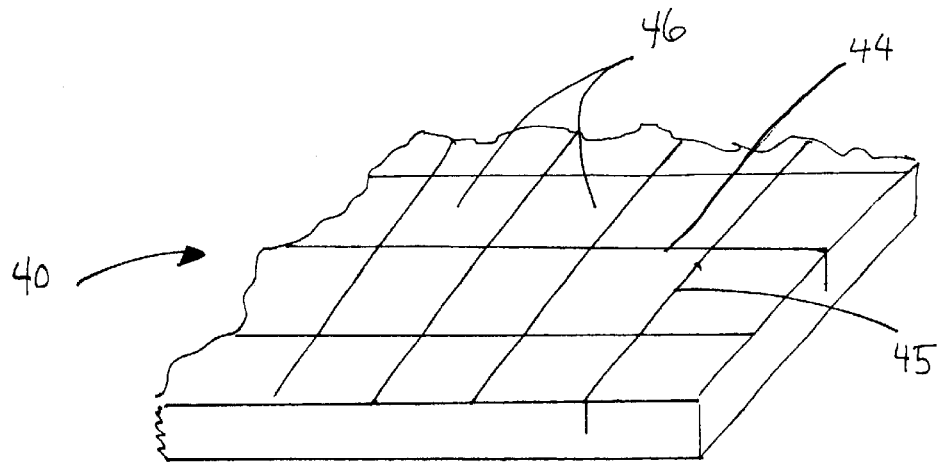
Figure 3C:
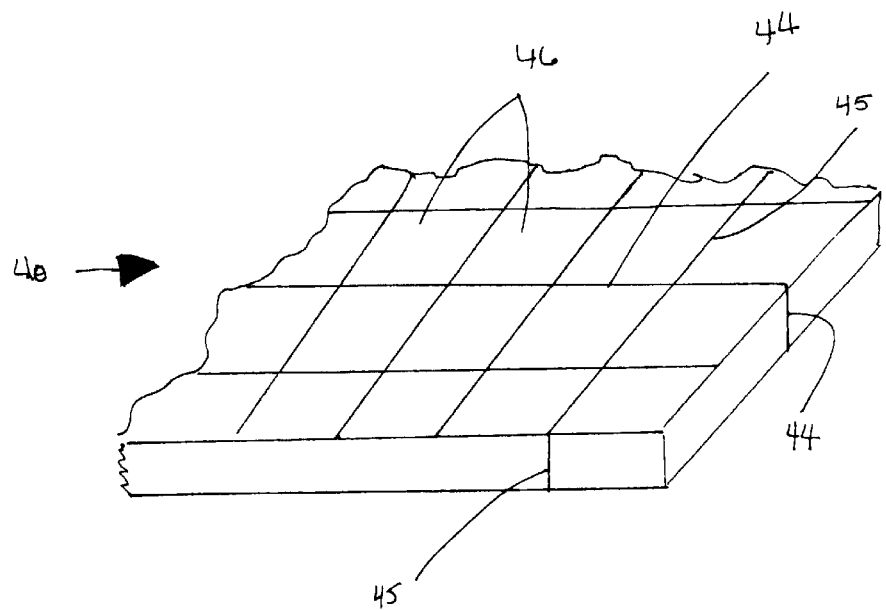

Referring to FIG. 3a, sheet 40 has an absorbent structure 42 having top surface 42a with lines of weakness incorporated therein in a grid pattern of horizontal lines weakness 44 and vertical lines of weakness 45. In one embodiment, lines of weakness 44, 45 are slits extending partially or entirely through the thickness of the absorbent structure 42. Such lines of weakness 44, 45 aid dispersibility of the plurality of discrete sections 46 of absorbent structure 42. Referring to FIG. 3b, an enlarged partial perspective view of sheet 40 of FIG. 3a is shown, wherein sheet 40 comprises lines of weakness 44, 45 that extend partially through the thickness of absorbent structure 42. Referring to FIG. 3c, an enlarged partial perspective view of sheet 40 of FIG. 3a is shown, wherein sheet 40 comprises lines of weakness 44, 45 that extend entirely through the thickness of absorbent structure 42. Preferably the lines of weakness in this embodiment extend through the entire thickness of the absorbent structure 42. The bottom surface (not shown) of absorbent structure 42, including the plurality of sections 46, is adhered to a barrier layer such as a water soluble polymeric film as previously described (preferably polyvinyl alcohol). The barrier layer can be applied in the same manner as shown and described in connection with FIG. 4, such that it is oriented across the horizontal plane of the sheet 40. Preferably, for sheets intended for flushing down urinals or other drain orifices of relatively small size, the discrete sections.

A preferred embodiment of the present invention has a construction as shown in FIG. 3a, wherein the absorbent structure preferably, although not necessarily, is made from cellulosic fibers which are relatively short, such as hardwood fibers or a blend of fibers having a short average fiber length, such fibers or blend of fibers having average fiber lengths of about 4 mm or less, more preferably about 3 mm or less, more preferably about 2 mm or less. The preferred barrier layer for such purposes is a polymeric film, such as previously described. Such barrier layers can provide adequate extensibility during ring rolling to retain integrity without tearing, and therefore continue to provide tensile strength to the absorbent product once processing is done.

In another preferred embodiment corresponding to FIG. 3a, the lines of weakness 44, 45 are continuous lines of partially disentangled fibers further characterized by being low density regions compared to the adjacent regions of non-mechanically weakened regions of fibers. Such lines of weakness 44, 45 aid in rapid dispersing of the product into individual fibers, or small chunks, agglomerations, or sections of fibers, or a combination thereof. Alternately the absorbent structure can be considered as having a plurality of low density regions disposed in a pattern (random or, in this specific embodiment, non-random) separated by higher tensile strength regions. Preferably the absorbent structure described above comprises long fibers, such as softwood fibers, especially chemically pulped softwood fibers, or a blend of softwood and hardwood fibers. Preferably such structures will contain at least about 25% softwood fibers, more preferably at least about 50% softwood fibers, most preferably at least about 80% softwood fibers. The relative proportions of types of softwood fibers are as previously discussed. The average fiber length is preferably at least about 2 mm, more preferably at least about 2.25 mm, most preferably at least about 2.5 mm. The upper limit average fiber lengths are as previously discussed.

Referring to FIG. 6, shown is an alternate set of cylindrical ring rolls 550 having upper ring roll 552 and lower ring roll 554, each with rows 555 of teeth 556. Rows 555 cylindrically extend around the circumference of the rolls 552, 554, about axis C'–C". Rows 555 are separated by inactive grooves 558. Teeth 556 have ridge lines 556a which extend in a direction parallel to the axis C'–C". Grooves 558 are optional and not essential for purposes of this invention. Optionally, teeth 556 can extend continuously along the width of the ring roll without grooves or other interruption to the teeth 556 or teeth ridge lines 556a. Ring rolls 550 can have the same range of teeth spacing, depth, and degree of engagement during use as described above.

In a preferred process for making absorbent products of the present invention, the absorbent structure is ring rolled by at least two sets of ring rolls wherein one set of ring rolls ring has teeth extending in a direction perpendicular to the longitudinal axis of the roll, such as shown in FIG. 5, and another set of ring rolls has teeth extending in the direction parallel to the longitudinal axis of the roll, such as shown in FIG. 6.

Each ring rolling step of the present invention imparts lines of weakness in the absorbent product in a direction parallel with the teeth of the ring rolls. Thus, by using ring rolls that impart a plurality of perpendicular lines of weakness (i.e., a first set of lines of weakness in a horizontal direction and a perpendicular set of lines of weakness in a vertical direction, such as shown in FIG. 3), an absorbent structure having a grid pattern of lines of weakness can be provided.

In the above processes, when notched tooth ring rolls are used in one of the two opposing ring rolls of the set to make absorbent products having an absorbent structure and a barrier layer, such as a polymeric material, preferably the notched ring roll directly contacts the absorbent structure and the un-notched ring roll directly contacts the barrier layer. In the preferred process for making the product as shown in FIG. 3, the second set of ring rolls are as shown in FIG. 6 except with ridge lines of teeth that extend continuously along the axis of the ring roll, i.e. without being separated into separate rows of teeth.

Noncontinuous regions of weakness can be provided by ring rolling with rolls having a plurality of notches along the perimeter of the teeth. Such notched teeth can be used for ring rolling in one direction or a plurality of directions upon the absorbent structure, for example wherein the second application of ring rolling is perpendicular to the first. Further combinations of notched teeth and non-notched teeth can be used for the separate ring rolling teeth. Further, the teeth during any specific ring rolling step can include a combination of notched and non-notched teeth.

Figure 9:
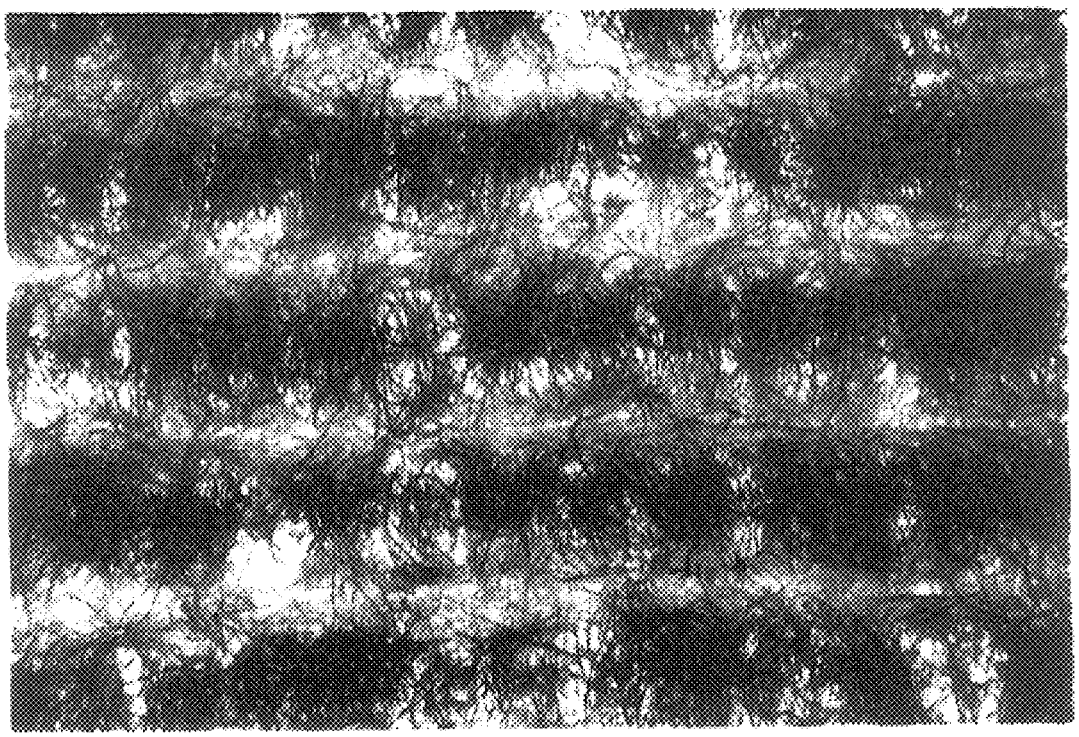
FIG. 9 is a 4× magnified photograph showing a top planar view of an embodiment of the present invention.
Figure 10:
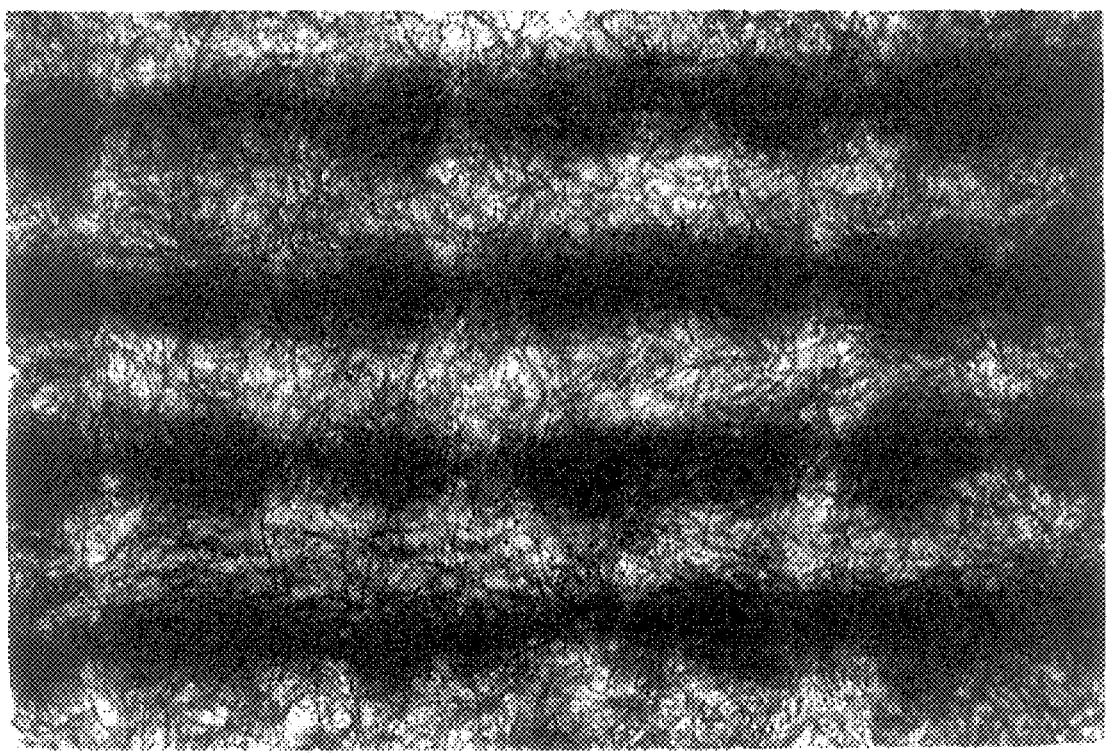
FIG. 10 is a 4× magnified photograph showing a bottom planar view of the product of FIG. 9.
Figure 11:
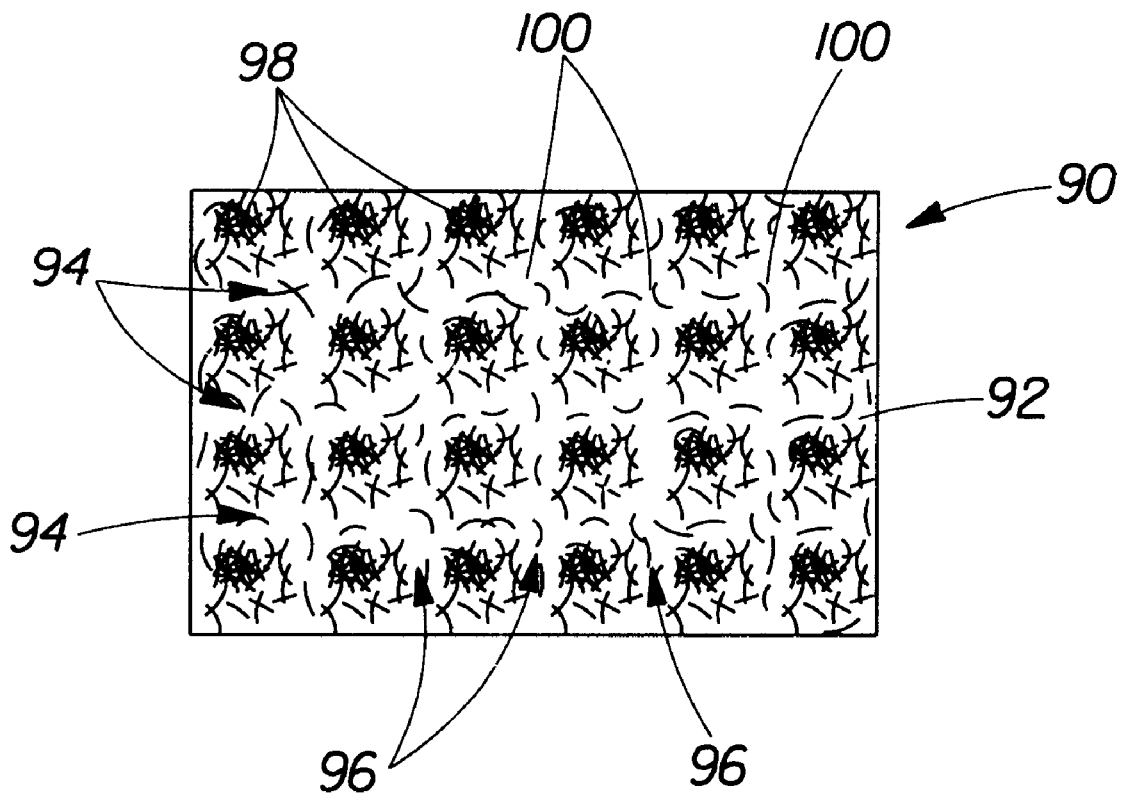
FIG. 11 is a bottom planar view drawing of an embodiment of the present invention of the type shown in FIGS. 9 and 10.

FIGS. 9 and 10 are photographs exemplifying a preferred embodiment of the present invention that can be made by ring rolling an absorbent product in two directions, one direction perpendicular to the other, to form a pattern of regions of weakness that are parallel lines of partially detangled fibers (shown in FIGS. 9 and 10 as light colored parallel lines running horizontally across the photographs). Less distinct but still observable are a series of parallel, vertical lines of partially detangled fibers, also appearing as light colored regions. FIG. 9 shows a top planar view. FIG. 10 shows a bottom planar view. Although not distinctly shown in the photograph of FIG. 10, the bottom surface can have a polymeric barrier film layer. The darker regions correspond to portions of the absorbent structure that are not partially detangled by the ring rolling steps. The horizontal lines of weakness in FIGS. 9 and 10 would generally be formed by the second of the two, sequential ring rolling steps, while the less prominently observable vertical lines of weakness would generally be formed by the first of the ring rolling steps. FIG. 11 is a drawing showing a top planar view of the preferred embodiment of an absorbent product 90, such as the type of product shown in FIGS. 9 and 10, having an absorbent fibrous structure 92, with non-detangled regions 98 separated by horizontal regions of partially detangled fibers 94 and vertical regions of partially detangled fibers 96. The intersection regions 100 of the horizontal and vertical regions of partially detangled fibers 94, 96 will as a result of the two ring rolling steps be partially disentangled in both horizontal and vertical directions. Absorbent products as shown in FIGS. 9–11 can be made using softwood fibers or other relatively long fibers, or blends of such long fiber types with hardwood fibers. The preferred ranges of such blends are discussed above. Especially preferred is a blend comprising 15% hardwood kraft (e.g., Eucalyptus), 40% NS CTMP, and 45% SSK.

In addition to bi-layer products, it is also contemplated that other multi-layer products can be used and prepared in accordance with the present invention. These can include, without limitation, tri-layer sheets having two outer barrier layers with an inner absorbent structure.

The products of the present invention can be used for a wide variety of purposes including but not limited to: absorption of residual urine from males; residual urine from females; toilet paper (e.g., for wiping bowel movement remains away from the body) and other wipes and absorbent products for bowel movements, urine and other bodily fluids; household and hard surface cleaning wipes such as but not limited to glass cleaners, kitchen cleaning, furniture cleaning, bathroom cleaning; industrial cleaning and fluid absorption products including any hard surface cleaning applications as well as chemical spill; personal care applications such as skin and facial cleaning, and application and/or removal of cosmetics and/or conditioners and/or health care actives to the skin; cleaning and/or wiping of clothes and textiles; baby care applications such as bibs, and diapers; and health care applications such as bandages. Products hereof can be in a variety of shapes and sizes. The preferred products will be in the form of sheets. Such sheets can further be in a variety of shapes and sizes, and further can be in the form of semi-enclosed products, such as mitts or gloves, having an exterior comprising the absorbent sheet of the present invention, an interior region, and an opening through which a hand, finger, or body appendage or device may be inserted. Such semi-enclosed products can be made by attaching two parallel sheets to one another at the edges, such as by adhesives, while allowing at least one section of the edges to remain non-adhered, thereby providing an opening through which appendages or devices may be inserted.

Additives can be included in the absorbent products hereof, including without limitation absorbent polymeric gelling materials (such as partially cross-linked polyacrylic acids/acrylates), anti-bacterials, deodorants, fragrances, odor absorption ingredients (e.g. cyclodextrins), dyes, and skin conditioning agents.

METHOD OF USE

A preferred method of using the absorbent products of the present invention comprises the steps of: (a) optionally, and preferably, dispensing an absorbent product of the present invention from a dispenser (such as but not limited to a package or a wall or urinal mounted device capable of containing a plurality of individual absorbent products); Preferably the absorbent product is in the form of a sheet sized as previously described; (b) urinating into a urinal either before of after dispensing the absorbent product; (c) subsequent to dispensing the absorbent product and urinating, contacting the body at the point of urine excretion with the absorbent product; (d) depositing the absorbent product in the urinal. Preferably the urinal is subsequently flushed. Flushing can be done by the person who has urinated or is accomplished automatically by a flushing mechanism of the urinal. Automated flushing mechanisms of urinals include various types. One type is a continuously flushing urinal. A second type is a periodically flushing urinal. Yet a third type is a urinal having a sensor which senses when a person enters and/or leaves the vicinity of the urinal and triggers a flushing mechanism one the user has departed from the area.

The above methods can also be adapted for use by persons using toilets instead of urinals, including both males and females.

DISPENSING DEVICES

The present invention further provides a dispensing device containing at least two absorbent products, preferably 3 or greater, of the present invention. Such products are removably contained in the dispensing device. Such dispensing device can be a package, such as shown but not limited to the package of FIG. 7, wherein package 100 contains body 102 and lid 104. Inside the package 100 is a containment region 105 suitable for containing a plurality of absorbent products. The portion of the body 102 of the package 100 that is exposed when the lid 104 has an open cut-away region 106 to allow easy access for dispensing of the absorbent product 60 with one hand. Lid 104 can be closed by folding along fold lines 108, 110. Lid 104 has window 112 that can contain an adhesive sheet with adhesive material facing toward and contacting the front face 114 of the body 106 when the lid 104 is closed. Package can be constructed of cardboard or other suitable packaging material. Other types of packages can also be used including, without limitation, wraps of flexible polymeric films.

Another type of dispensing device is a structure that contains two or more absorbent products of the present invention that is disposed permanently or temporarily in the vicinity of a toilet or, especially, a urinal. Such a device can be located in a user-reachable location while attending to the urinal or toilet, or alternately can be located in any convenient position for the user to dispense the absorbent product prior to urinating. For example, the dispensing device can be located at any point along the path by which a potential user walks on the way to using the urinal or toilet. The disposing device can, for example, be mounted on a wall, divider, or shelf, or on the urinal or toilet, or on a separate stand, or on any other surface, in the user-reachable vicinity of the urinal or toilet. Preferably it is mounted or positioned within about 2 meters of the urinal or toilet, more preferably within about 1 meter, most preferably within about 0.75 meters. Alternately it can be mounted in similar fashion in bathroom, restroom, or lavatory. The package 100 of FIG. 7, for example, can be used for this aspect of the invention by placing it in the desired position and optionally attaching it to a surface, such as with an adhesive. The lid 104 can optionally be removed. The package 104 can optionally have perforations to facilitate removal of the lid, such as along the border 105 of the lid 104 adjacent to the body 102.

Figure 8:
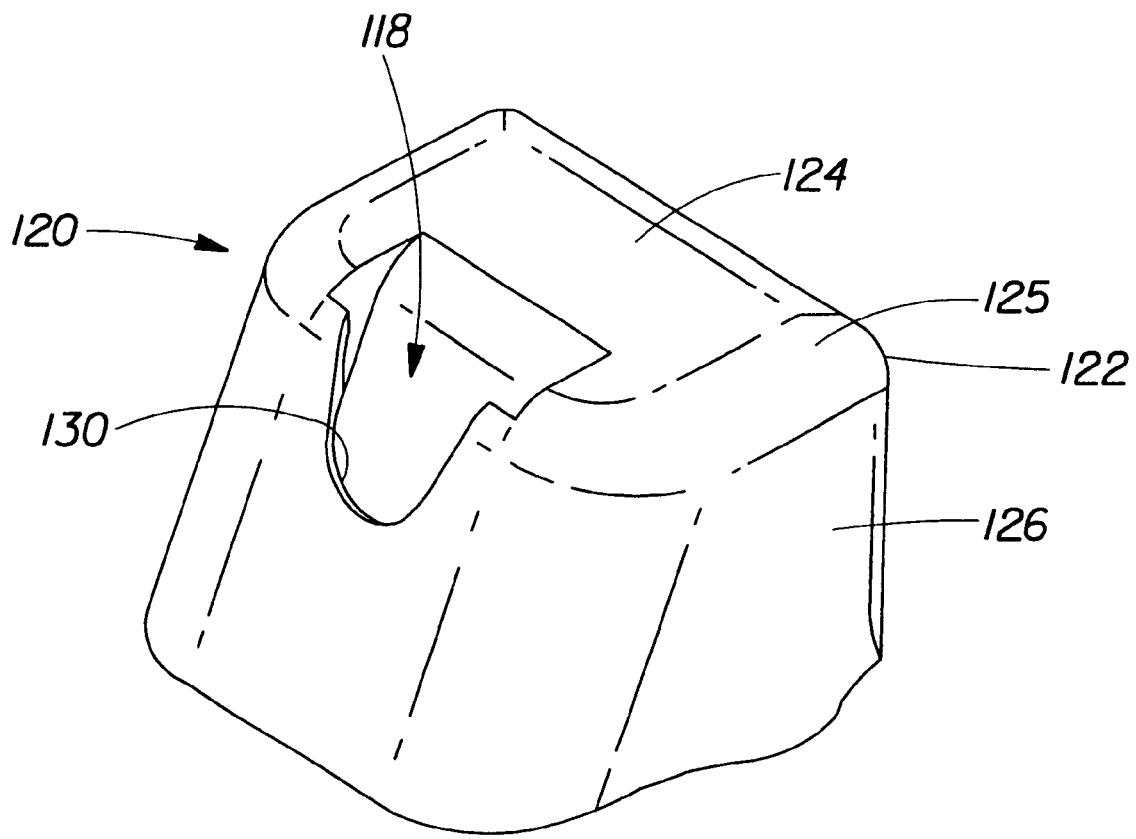
FIG. 8 shows a device suitable for containing and dispensing absorbent products of the present invention or packages containing absorbent products of the present invention.

FIG. 8 shows an alternate dispensing device 120 suitable for placement and/or attachment in the vicinity of a urinal or other flushing device. Dispensing device 120 has body 122 comprising a top surface 124 with beveled edge 125, skirt 126 with a semi-enclosed recess 128 suitable for containing absorbent products of the present invention. In FIG. 8, recess 128 is integral with skirt 126. Alternately, the recess can be integral with the top surface, or can be appended to the skirt or top surface. Semi-enclosed recess 128 has an opening with a cut-away region 130 to facilitate insertion (such as in connection with refilling the device), and removal of the absorbent products prior to use, such as but not limited to absorbing residual urine or other intended material.

Figure 7:
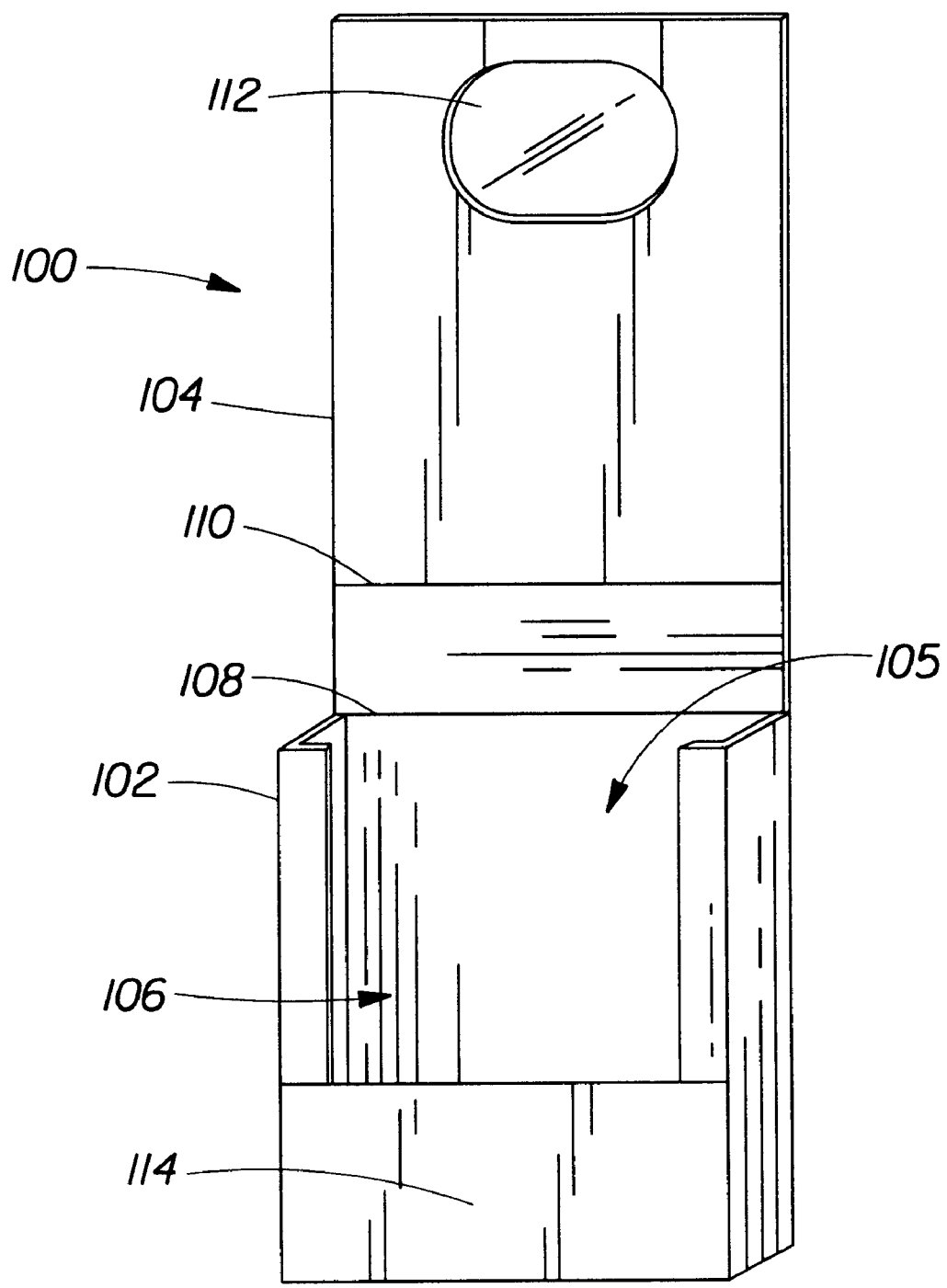
FIG. 7 shows a package suitable for containing and dispensing absorbent products of the present invention.

It is especially desirable to store absorbent products of the present invention in such semi-enclosed regions as shown by example in FIGS. 7 and 8 when the absorbent products comprise a polymeric barrier layer, such as but not limited to polyvinyl alcohol, which can dry out upon extended exposure to the atmosphere and subsequently become brittle.

As used herein, rolls, strips, or other sheets of absorbent product separated by lines of weakness intended to separate into sub-divide into two or more individual products shall be considered herein as comprising the number of absorbent products into which the roll is intended to divide prior to use.

TEST METHODS

Rate of Dispersibility

Rate of Dispersibility is determined according to a modified Japanese Industrial Standard (JIS) test P4501-1993. An 800 ml cylindrical graduated Griffin beaker (6.3 cm by 15.2 cm, such as VWR Scientific Products, Catalogue # 13910-267, 1997/1998) with 300 ml water deionized (DI) water at 23 degrees C is equipped with a 35 mm diameter magnetic starhead stir disk (12 mm maximum thickness, starhead protrusions extending from both sides, such as available from VWR Scientific Products, catalogue # 58948-568, 97/98, or equivalent), and placed on a magnetic stir plate set to rotate the stir disk at 600 revolutions per minute (rpm).

A 0.38 g sample of absorbent product is pre-conditioned at 20 degrees C (+/−5 degrees C) and 65% Relative Humidity (+/−5%) until equilibrium. In the event that the product to be tested is less than 0.38 g, then multiple products or fractions of multiple products are used to increase the total weight to 0.38 g. In the event that the product to be tested is larger than 0.38 g, then product size is reduced such that a 0.38 g portion of the product is tested. The product sample tested according to the present test should have a total exterior surface area of at least 20 $cm^2$. If the total exterior surface area of a product sample that has been reduced to 0.38 g is less than 20 $cm^2$, then a larger sample of the product should be used for the present test such that the total surface area is 20 $cm^2$.

The sample is dropped into the center of the vortex caused by the stirring, which causes stir bar rotational rate to decrease, and a stopwatch is simultaneously started. The time in seconds for the stir bar to increase in rotational rate until it reaches 540 rpm is recorded as the Rate of Dispersibility. If addition of the sample to the beaker causes the stir disk to be moved off center from its natural axis of rotation or if it ceases rotating, the test run is invalid and should be repeated with a new sample of product.

Residual By-Product

Set-Up: A cylindrical USA Standard Testing Sieve (A.S.T.M. E-11 Specification) having square openings of 0.250 inches on each side (about 6.3 MM) with an 8.0 inch (20.3 cm) radius and 2.0 inch (5.1 cm) maximum, center depth (such as available from VWR Scientific Products, Catalogue # 57334-425, 87/98, or equivalent) is placed on a horizontal surface with a drain or receiving vessel underneath. A 147 mm diameter polypropylene powder funnel (such as available from VWR Scientific Products, Catalogue # 30252-957, 97/98, or equivalent) is suspended perpendicularly to the horizontal surface from a ring stand with the bottom edge of the funnel output tube 2.5 cm above the center of he sieve and the outer edge of the funnel output tube 7.6 cm from the edge of the sieve.

Test: A 0.38 g sample of absorbent product is pre-conditioned at 20 degrees C (+/−5 degrees C) and 65% Relative Humidity (+/−5%) until equilibrium. In the event that the product to be tested is less than 0.38 g, then multiple products or fractions of multiple products are used to increase the total weight to 0.38 g. In the event that the product to be tested is larger than 0.38 g, then product size is reduced such that a 0.38 g portion of the product is tested. The product sample tested according to the present test should have a total exterior surface area of at least 20 $cm^2$. If the total exterior surface area of a product sample that has been reduced to 0.38 g is less than 20 $cm^2$, then a larger sample of the product should be used for the present test such that the total surface area is 20 $cm^2$.

An 800 ml cylindrical graduated Griffin beaker (6.3 cm by 15.2 $cm^2$, such as available from VWR Scientific Products, Catalogue # 13910-267, 1997/1998) with 300 ml water deionized (DI) water at 23 degrees C and equipped with a 35 mm diameter magnetic starhead stir disk (12 mm maximum thickness, starhead protrusions extending from both sides, such as available from VWR Scientific Products, catalogue # 58948 568, 97/98, or equivalent) is provided and placed on a magnetic stir plate set to rotate the stir disk at 350 revolutions per minute (rpm). The sample is dropped into the center of the vortex caused by the stirring and a stopwatch is simultaneously started. At 15 seconds, the stirring is stopped and the stir disk is removed from the beaker. If addition of the sample to the beaker causes the stir disk to be moved off center from its natural axis of rotation or if it ceases rotating, the test run is invalid and should be repeated with a new sample of product. The beaker contents are immediately poured into the funnel. A 50 ml aliquot of DI water is added to the beaker and swirled to rinse any remaining sample residue from the beaker surfaces and then poured down the funnel. Sample residue of the slurry that remains on the top surface of the sieve is removed and placed on a pre-weighed metal sheet or pan (e.g. aluminum foil or pan), and dried at 82 degrees C for 2 hours. The sample is then cooled to room temperature and weighed. The percentage residue is calculated as [(weight of dried residue plus foil—weight of foil)/(original weight of dry product or sample)] X 100.

Drop Acquisition Test

A 0.38 g sample of absorbent product is pre-conditioned at 20 degrees C (+/−5 degrees C) and 65% Relative Humidity (+/−5%) until equilibrium. In the event that the product to be tested is less than 0.38 g, the product is tested as is. In the event that the product to be tested is larger than 0.38 g, then a 0.38 g portion of the product is tested. The product sample tested according to the present test should have a total exterior surface area of no greater than 60 $cm^2$. If the total exterior surface area of a product sample is greater than 60 $cm^2$, then a smaller sample of the product should be used for the present test such that the total surface area is 60 $cm^2$. Sample shapes of sheet products should adjusted to be square if possible. If the sample is not square, a rectangular sample (or a shape as close to rectangular as possible) should be prepared.

The sample secured by adhesive or two-sided tape on a clean flat rectangular working surface (e.g., a board) inclined at a 34 degree angle, relative to the horizontal. The sample is placed at an orientation with one edge of the sample parallel to the bottom edge of the working surface and the surface or area of the sample intended for fluid acquisition or direct contact with objects or surfaces to be treated facing upward. If the sample is not square, the sample should be placed on the angled working surface (discussed below) with the shortest side parallel to the planar gravitational direction of flow of fluid (upon application of fluid to the sample as provided below). 0.50 ml of fluid at 23 degrees C is delivered from a hand held auto-pipette with the tip placed 0.6 cm above the center of the top-facing surface of the sample. The fluid is delivered quickly in a period of 1 second or less. The operator observes whether the fluid was contained or whether the product experienced fluid escaping or running off the sample.

The products of the present invention will preferably not experience fluid run off using DI water. Products intended for absorption of urine will preferably not experience fluid run off using the Synthetic Urine formulation disclosed below in this Test Methods section. Products intended for absorption of other fluids will preferably not experience run off when tested with the types of fluids which they are specifically intended to absorb.

Pore Volume Distribution (PVD) Test

Principle:

Pore volume distribution for a sample is measured down to a pore size (radius) of about five microns using the Textile Research Institute (Princeton, N.J.) Liquid Porosimeter. This instrument (i) applies pre-selected, generally incremental, hydrostatic pressures to a sample pad that can absorb/desorb fluid through a fluid-saturated membrane and (ii) determines the incremental and cumulative quantity of fluid that is absorbed/desorbed by the pad at each pressure. A weight is positioned on the sample to ensure good contact between sample and membrane and to apply an appropriate mechanical confining pressure. A fluid having a suitable surface tension ($\gamma$) is used to ensure wettability (cos ($\theta$)=1) of the absorbent structure surfaces. Deionized water (Surface tension approximately 72 dyes/cm) is used as the fluid as long as the above wettability requirement is met. For absorbent products intended to absorb urine, the Synthetic Urine formulation shown herein can also be used. Preferably, for specialized absorbent products intended to absorb specific types of fluids, or made from absorbent material which are not as highly hydrophilic as cellulosic fibers, or for which water does meet the above criteria, the fluid utilized should be chosen or modified such that it wets the structure in accordance with the above.

Each sample evaluation comprises an absorption/desorption cycle. In the absorption sequence cumulative volume absorbed versus incrementally decreasing hydrostatic pressure is measured. This is followed by a single desorption sequence where cumulative volume desorbed versus incrementally increasing hydrostatic pressure is measured. Hydrostatic pressures (P) range from a high pressure corresponding to an equivalent radius:

$r=2\gamma \cos (\theta)/P$ of approximately five microns to a zero or near-zero pressure corresponding to an equivalent radius at least about 1000 microns or greater.

Additional detail is provided by the following references:
1. A. Burgeni and C. Kapur, Capillary Sorption Equilibria in Fibrous Masses, Textile Research Journal 37, 356 (1967).
2. H. G. Heilweil, ed., Determining Pore Size Distributions in Fibrous Materials, Notes on Research, Textile Research Institute, Number 363 (April 1984).
3. B. Miller and I. Tyomkin, An Extended Range Liquid Extrusion Method for Determining Pore Size Distribution, Textile Res. J. 56,35 (1986).

Apparatus:
Porosimeter (Available from Textile Research Institute of Princeton, N.J. as Model LP-5)
Membrane: MILLIPORE 0.80 $\mu$M pore size GS Filter 90 mm (Available from Millipore Corp. of Bedford, Mass. as Catalog Number GSWP 090-25)
Procedure:
Sample Preparation:
Shortly before measuring pore volume distribution, the caliper of the sample is measured (as described herein) under a confining pressure of 0.2 psi (1.4 kPa). Sample density is calculated from the weight, caliper, and area of the sample.
Confining Pressure:
A confining pressure of 0.2 psi (1.4 kPa) is used for the pore-volume distribution measurement. The same or equivalent weight that is used for determining sample density is also used for applying the confining pressure during the pore volume measurement.
Instrumentation Configuration:
Set up the porosimeter according to the instruction manual.
Absorption/Desorption Cycle Characteristics:
An absorption/desorption cycle comprises two steps. First, a single absorption sequence where cumulative volume absorbed versus incrementally decreasing hydrostatic pressure is measured. This is followed by a single desorption sequence where cumulative volume desorbed versus incrementally increasing hydrostatic pressure is measured. Hydrostatic pressures range from a high pressure corresponding to an equivalent radius of approximately five microns to a zero or near-zero pressure corresponding to an equivalent radius at least about 1000 microns or greater.
Absorption/Desorption Procedure for an Initially Dry Sample:
1. Input parameters are entered as described in the equipment instructions and the controlling computer program is started.
2. The top of the instrument test cell is secured and the vent valve is shut. The liquid flow valve to the balance is opened. At this step the sample is not yet in the test cell.
3. The controlling computer program is continued. The hydrostatic pressure adjusts to a pre-set value (i.e., STOP RADIUS) that is slightly higher than the first inputted pressure used in the experiment.
4. After equilibration is signaled, the liquid valve to the balance is shut, the test cell is opened, the sample is positioned on the membrane, the confining weight is positioned on the sample, and the top of the instrument test cell is secured.
5. The program is continued and hydrostatic pressure adjusts to first inputted pressure.
6. After equilibration is signaled, the fluid valve to balance is opened.
7. The sample is cycled through a predetermined series of pressures which correspond to specific equivalent pore radii.
Blank Subtraction:
A blank run is recorded, as above, but with the test cell empty. This determines the background absorption/desorption response of the system and membrane. Values for cumulative absorption and desorption volumes versus hydrostatic pressure are obtained. These values are used to correct the corresponding values measured for the sample.
Calculation of Normalized Cumulative Volumes:
Based on the incremental volume values, the controlling computer program calculates blank-corrected values for cumulative volume versus equivalent pore radius. Cumulative volumes are divided by the dry weight of the pad and reported in units of mm³/mg. Cumulative volumes are divided by the volume at saturation (i.e., the cumulative volume measured for the largest equivalent radius at zero or near-zero pressure) to obtain the normalized cumulative volume (expressed as %) versus equivalent pore radius. Values for 0 cm hydrostatic head, PVD(0), and 7 cm hydrostatic head, PVD(7), are measured and recorded. PVD(0) is measured at the end of the absorption cycle. PVD(7) is measured as peak absorption on the absorption side of the absorption/desorption cycle.

Strikethrough Test

The following test is used to measure Strikethrough Resistance of absorbent products of the present invention.

A 0.38 g sample of absorbent product is pre-conditioned at 20 degrees C (+/−5 degrees C) and 65% Relative Humidity (+/−5%) until equilibrium. In the event that the product to be tested is less than 0.38 g, the product is tested as is. In the event that the product to be tested is larger than 0.38 g, then a 0.38 g portion of the product is tested. The product sample tested according to the present test should have a total exterior surface area of no greater than 60 cm². If the total exterior surface area of a product sample is greater than 60 cm², then a smaller sample of the product should be used for the present test such that the total surface area is 60 cm².

A WHATMAN™ Qualitative Filter #1 (available from VWR Scientific Products, Catalogue # 28450-160, 1997/1998, or equivalent) is placed on a flat, horizontal glass or plexiglass surface. The product sample is placed on the filter paper. If the sample as a barrier layer, the barrier layer is upward. A solution of 0.3 ml DI water with 500 ppm FD&C Blue Dye #2 food color is applied to the center of the sample with an auto-pipette in less than 1 second from a height of the tip of the auto-pipette about 0.6 cm above the upper surface of the sample. A weight is immediately applied covering the upper surface of the sample that applies 0.20 psi to the surface (about 70.4 g/cm²). After the desired predetermined period (e.g., 2 seconds, 10 seconds, or 30 seconds), the weight product sample are removed from the filter paper and the filter paper is inspected to determine if it contains any wetness stains. Absence of wetness stains signifies absence of fluid strikethrough. A product not experiencing strikethrough within a specific period of time is referred to herein as having Strikethrough Resistance of at least that particular period of time, for example Strikethrough Resistance of at least 2 seconds, at least 10 seconds, or at least 30 seconds.

Synthetic Urine Formulation

The following formula is used for synthetic urine used in Test Methods of the present invention:

| Compound | MW | Concentration (g/l) |
|---|---|---|
| KCl | 74.6 | 2.00 |
| Na2SO4 | 142 | 2.00 |
| (NH4)H2PO4 | 115 | 0.85 |
| (NH4)2HPO4 | 32 | 0.15 |
| CaCl2—2H2O | 147 | 0.25 |
| MgCl2—6H2O | 203 | 0.50 |
| DI Water | | q.s. |

Surface Tension: approximately 70 dynes/cm

While particular embodiments of the present invention have been illustrated and described, it would be obvious to those skilled in the art that various other changes and modifications can be made without departing from the spirit and scope of the invention.

What is claimed is:

1. An absorbent product comprising an absorbent structure, said absorbent product having a Rate of Dispersibility of about 60 seconds or less and a Strikethrough Resistance of at least 2 seconds.

2. An absorbent product as in claim 1, wherein said Rate of Dispersibility is about 30 seconds or less and said Strikethrough Resistance is at least about 10 seconds.

3. An absorbent product as in claim 2, wherein said Rate of Dispersibility is about 25 seconds or less and said Strikethrough Resistance is at least about 10 seconds.

4. An absorbent product as in claim 3, wherein said Rate of Dispersibility is about 15 seconds or less.

5. An absorbent product as in claim 4, wherein said Strikethrough Resistance is at least about 30 seconds.

6. An absorbent product as in claim 1, wherein said absorbent structure comprises a sheet of absorbent fibers.

7. An absorbent product as in claim 2, wherein said absorbent fibers are cellulosic fibers.

8. An absorbent product as in claim 6, wherein said absorbent product further comprises a water soluble barrier layer barrier attached to said absorbent structure.

9. An absorbent product as in claim 8, wherein said water soluble barrier layer is a water soluble polymeric film.

10. An absorbent product comprising an absorbent structure, said absorbent product having a Rate of Dispersibility of about 60 seconds or less and a Drop Acquisition Volume of at least about 0.05 ml and said absorbent structure having a PVD(0) of at least 2 g /g absorbent structure.

11. An absorbent product as in claim 10, wherein said Rate of Dispersibility is about 30 seconds or less, said Drop Acquisition Volume is at least about 0.1 ml, and said PVD(0) is at least about 2.5 g/g absorbent structure.

12. An absorbent product as in claim 11, wherein said Rate of Dispersibility is about 25 seconds or less, said Drop Acquisition Volume is at least about 0.5 ml, and said PVD(0) is at least about 3 g/g absorbent structure.

13. An absorbent product as in claim 12, wherein said Rate of Dispersibility is about 15 seconds or less.

14. An absorbent product as in claim 13, wherein said Drop Acquisition Volume is at least about 1.0 ml.

15. An absorbent product as in claim 10, wherein said absorbent structure comprises a sheet of absorbent fibers.

16. An absorbent product as in claim 15, wherein said absorbent fibers are cellulosic fibers.

17. An absorbent product as in claim 15, wherein said absorbent product further comprises a water soluble barrier layer barrier attached to said absorbent structure.

18. An absorbent product as in claim 17, wherein said water soluble barrier layer is a water soluble polymeric film.

19. An absorbent product comprising an absorbent structure, said absorbent product having a Rate of Dispersibility of about 120 seconds or less, a Strikethrough Resistance of at least 10 seconds, and a Drop Acquisition Volume of at least about 0.1 ml.

20. An absorbent product as in claim 19, wherein said Rate of Dispersibility is about 60 seconds or less and said Drop Acquisition Volume is at least about 0.5 ml.

21. An absorbent product as in claim 20, wherein said Rate of Dispersibility is about 30 seconds or less.

22. An absorbent product as in claim 21, wherein said Rate of Dispersibility is about 25 seconds or less.

23. An absorbent product as in claim 22, wherein said Rate of Dispersibility is about 15 seconds or less said Drop Acquisition Volume is at least about 1.0 ml.

24. An absorbent product as in claim 23, wherein said Strikethrough Resistance is at least 30 seconds.

25. An absorbent product as in claim 19, wherein said absorbent structure comprises a sheet of absorbent fibers.

26. An absorbent product as in claim 25, wherein said absorbent fibers are cellulosic fibers.

27. An absorbent product as in claim 25, wherein said absorbent product further comprises a water soluble barrier layer barrier attached to said absorbent structure.

28. An absorbent product as in claim 27, wherein said water soluble barrier layer is a water soluble polymeric film.

29. An absorbent product comprising:
i. an absorbent fibrous web;
ii. a water soluble polymeric barrier layer connected to said web;
wherein at least said absorbent fibrous web is mechanically weakened, wherein said product a basis weight in the range of from about 50 g/m$^2$ to about 250 g/m$^2$, and wherein said product has a Rate of Dispersibility of about 120 seconds or less and a Strikethrough Resistance of at least about 2 seconds.

30. An absorbent product as in claim 29, wherein said absorbent fibrous web comprises cellulosic fibers.

31. An absorbent product as in claim 29, wherein said absorbent fibrous web is a ring rolled fibrous web.

32. An absorbent product as in claim 29, wherein said product has a Rate of Dispersibility of about 30 seconds or less.

33. An absorbent product as in claim 32, wherein said Rate of Dispersibility is about 15 seconds or less.

34. An absorbent product as in claim 29, wherein said water soluble polymeric barrier layer is a polymeric film.

35. An absorbent product as in claim 34, therein said polymeric film is laminated to said absorbent fibrous web.

36. An absorbent structure as in claim 35, wherein said polymeric film is polyvinyl alcohol.

37. An absorbent product as in claim 19, wherein said product is in the form of a sheet.

38. An absorbent product as in claim 37, wherein said web comprises a grid of horizontal and vertical lines of weakness.

39. An absorbent product as in claim 37, wherein said sheet has a basis weight of from about 60 g/m$^2$ to about 150 g/m$^2$.

40. An absorbent product as in claim 39, wherein said sheet has a basis weight of from about 70 g/m$^2$ to about 120 g/m$^2$.

41. An absorbent product as in claim 29, wherein said mechanically weakened web comprises a plurality of lines of weakness.

42. An absorbent structure as in claim 41, wherein said absorbent structure is a ring rolled fibrous web.

43. An absorbent product as in claim 41, wherein said absorbent product has a thickness in the range of from about 0.3 mm to about 5 mm, and wherein said lines of weakness are slits that extend throughout at least 50% of the thickness of said web.

44. An absorbent product as in claim 43, wherein said absorbent fibrous web comprises hardwood fibers.

45. An absorbent product as in claim 29, wherein said mechanically weakened web comprises partially disentangled fibers.

46. An absorbent structure as in claim 45, wherein said absorbent structure is a ring rolled fibrous web.

47. An absorbent product as in claim 45, wherein said lines of weakness comprise a plurality of lines of partially disentangled fibers.

48. An absorbent product as in claim 45, wherein said absorbent fibrous web comprises softwood fibers.

49. An absorbent product comprising:
i. an absorbent fibrous web;
ii. a water soluble polymeric barrier layer connected to said web;
wherein at least said absorbent fibrous web comprises a plurality of discrete sections comprising regions of weakness, said sections having a cross section that can be enclosed by a square having a side length of about 30 mm or less, wherein said product a basis weight in the range of from about 50 g/m$^2$ to about 250 g/m$^2$, and wherein said product has a Rate of Dispersibility of about 120 seconds or less and a Strikethrough Resistance of at least about 2 seconds.

50. An absorbent product as in claim 49, wherein said side length is about 6.5 cm or less.

51. An absorbent product as in claim 49, wherein said product is a sheet.

52. An absorbent product as in claim 49, wherein said side length is about 15 cm or less.

53. An absorbent product as in claim 49, wherein said product has a Rate of Dispersibility of about 30 seconds or less.

54. An absorbent product as in claim 53, wherein said Rate of Dispersibility is about 15 seconds or less.

55. An absorbent product as in claim 49, wherein said sections are separated by lines of weakness.

56. An absorbent product as in claim 55, wherein said absorbent product has a thickness in the range of from about 0.3 mm to about 5 mm, and wherein said lines of weakness extend through the entire thickness of said web.

57. An absorbent product as in claim 55, wherein said web comprises hardwood fibers.

58. A product suitable for absorbing residual urine, comprising:
A package;
At least two dispersible absorbent articles removably contained in said package, wherein said absorbent articles have a Rate of Dispersibility of about 60 seconds or less.

59. A product as in claim 58, wherein said package has a top planar surface area of from about 15 cm$^2$ to about 40 cm$^2$.

60. A product as in claim 58, wherein said articles have a Strikethrough Resistance of at least 10 seconds.

61. A product as in claim 58, wherein said package is attached to a surface within about 2 meter of a urinal or toilet.

62. A product as in claim 58, wherein said package is attached to a surface in a lavoratory.

63. A product as in claim 58, wherein said Rate of Dispersibility is about 30 seconds or less.

64. A product as in claim 63, wherein said Rate of Dispersibility is about 15 seconds or less.

65. A product as in claim 58, wherein said absorbent articles are sheets having a top planar surface area from about 10 cm$^2$ to about 200 cm$^2$.

66. A product as in claim 65, wherein said absorbent articles are sheets having a top planar surface area of from about 15 cm$^2$ to about 40 cm$^2$.

67. A product as in claim 65, wherein said package has a top planar surface area of from about 15 cm$^2$ to about 40 cm$^2$.

* * * * *

UNITED STATES PATENT AND TRADEMARK OFFICE
CERTIFICATE OF CORRECTION

PATENT NO. : 6,613,954 B1
DATED : September 2, 2003
INVENTOR(S) : James Cameron Horney et al.

It is certified that error appears in the above-identified patent and that said Letters Patent is hereby corrected as shown below:

Column 8,
Line 4, "referably" should be -- preferably --.

Column 23,
Line 58, "32" should be -- 132 --.

Column 25,
Line 31, "therein" should be -- wherein --.

Column 26,
Line 49, "meter" should be -- meters --.

Signed and Sealed this

Second Day of May, 2006

JON W. DUDAS
*Director of the United States Patent and Trademark Office*